(12) United States Patent
McClellan et al.

(10) Patent No.: US 8,758,348 B2
(45) Date of Patent: Jun. 24, 2014

(54) SYSTEMS AND METHODS FOR STERNUM REPAIR

(75) Inventors: William Thomas McClellan, Morgantown, WV (US); Johnny Chang, Providence, RI (US)

(73) Assignee: Figure 8 Surgical, Inc., Menlo Park, CA (US)

( * ) Notice: Subject to any disclaimer, the term of this patent is extended or adjusted under 35 U.S.C. 154(b) by 19 days.

(21) Appl. No.: 12/727,212

(22) Filed: Mar. 18, 2010

(65) Prior Publication Data

US 2011/0022050 A1     Jan. 27, 2011

Related U.S. Application Data

(60) Provisional application No. 61/161,515, filed on Mar. 19, 2009, provisional application No. 61/252,145, filed on Oct. 15, 2009.

(51) Int. Cl.
| | |
|---|---|
| *A61B 17/56* | (2006.01) |
| *A61B 17/58* | (2006.01) |
| *A61B 17/82* | (2006.01) |
| *A61F 2/30* | (2006.01) |
| *A61B 17/06* | (2006.01) |

(52) U.S. Cl.
CPC ......... *A61B 17/823* (2013.01); *A61B 17/06066* (2013.01); *A61B 17/06166* (2013.01)
USPC .............. 606/74; 606/300; 606/215; 606/216

(58) Field of Classification Search
USPC ........... 606/215, 216, 74, 300–331, 228–233, 606/151–158; 600/37; 24/16 PB
See application file for complete search history.

(56) References Cited

U.S. PATENT DOCUMENTS

| | | | |
|---|---|---|---|
| 1,365,493 A | 1/1921 | Hedger | |
| 1,463,213 A * | 7/1923 | Hueseman | ........................ 2/324 |
| 1,950,799 A | 3/1934 | Jones | |
| 1,987,527 A | 1/1935 | Frank | |
| 2,089,474 A | 8/1937 | Glick | |
| 2,128,041 A | 8/1938 | Epstein | |

(Continued)

FOREIGN PATENT DOCUMENTS

| | | |
|---|---|---|
| JP | 62-295657 | 5/1989 |
| JP | 10-179605 | 7/1998 |

(Continued)

OTHER PUBLICATIONS

Synthes, Inc.; Technique Guide—Sternal ZipFix System; 26 pgs.; Jun. 2011.

(Continued)

*Primary Examiner* — Matthew Lawson
*Assistant Examiner* — Si Ming Lee
(74) *Attorney, Agent, or Firm* — Andrew D. Wright; Roberts Mlotkowski Safran & Cole, P.C.

(57) ABSTRACT

The invention provides systems and methods for sternum repair. A sternum repair device may include a central body, which may include a plurality of male and female components, such that a suture extends from a male component and is received by the female component. The suture may wrap around the sternum and the device may be tightened to keep the separate sternum pieces together.

28 Claims, 32 Drawing Sheets

(56) References Cited

U.S. PATENT DOCUMENTS

| | | | |
|---|---|---|---|
| 2,746,324 A | 5/1956 | Beardsley | |
| 2,981,994 A | 5/1961 | White | |
| 3,129,919 A | 4/1964 | Evans | |
| 3,258,040 A | 6/1966 | Evans | |
| 3,302,258 A * | 2/1967 | Meyer | 24/5 |
| 3,528,142 A | 9/1970 | Valdemar | |
| 3,570,497 A * | 3/1971 | Lemole | 606/151 |
| 3,584,525 A | 6/1971 | Caveney et al. | |
| 3,641,629 A | 2/1972 | Beardsley | |
| 3,661,187 A | 5/1972 | Caveney | |
| 3,837,373 A | 9/1974 | Beardsley | |
| 3,865,156 A | 2/1975 | Moody et al. | |
| 3,872,547 A | 3/1975 | Caveney et al. | |
| 3,946,769 A | 3/1976 | Caveney et al. | |
| 3,976,108 A | 8/1976 | Caveney et al. | |
| 4,004,618 A | 1/1977 | Turek | |
| 4,473,925 A | 10/1984 | Jansen | |
| 4,498,506 A | 2/1985 | Moody et al. | |
| 4,510,977 A | 4/1985 | Crowley | |
| 4,535,764 A | 8/1985 | Ebert | |
| 4,535,772 A * | 8/1985 | Sheehan | 606/218 |
| 4,570,340 A | 2/1986 | Shaw | |
| 4,607,867 A | 8/1986 | Jansen | |
| 4,646,591 A | 3/1987 | Jansen | |
| 4,730,615 A * | 3/1988 | Sutherland et al. | 606/215 |
| 4,813,416 A | 3/1989 | Pollak et al. | |
| 4,862,928 A | 9/1989 | Caveney et al. | |
| 4,887,334 A | 12/1989 | Jansen et al. | |
| 4,896,402 A | 1/1990 | Jansen et al. | |
| 4,896,668 A * | 1/1990 | Popoff et al. | 606/74 |
| 4,930,548 A | 6/1990 | Turek et al. | |
| D309,350 S | 7/1990 | Sutherland et al. | |
| 5,065,798 A | 11/1991 | Alletto et al. | |
| 5,072,738 A | 12/1991 | Wonder et al. | |
| 5,123,456 A | 6/1992 | Jansen | |
| 5,127,446 A | 7/1992 | Marelin | |
| 5,129,350 A | 7/1992 | Marelin | |
| 5,144,989 A | 9/1992 | Mika et al. | |
| 5,193,250 A | 3/1993 | Caveney | |
| 5,205,328 A | 4/1993 | Johnson et al. | |
| 5,286,249 A * | 2/1994 | Thibodaux | 602/12 |
| 5,303,571 A | 4/1994 | Quinn et al. | |
| 5,318,566 A | 6/1994 | Miller | |
| 5,322,091 A | 6/1994 | Marelin | |
| 5,330,489 A | 7/1994 | Green et al. | |
| 5,356,412 A | 10/1994 | Golds et al. | |
| 5,356,417 A | 10/1994 | Golds | |
| 5,366,461 A | 11/1994 | Blasnik | |
| 5,368,261 A | 11/1994 | Caveney et al. | |
| 5,386,856 A | 2/1995 | Moody et al. | |
| 5,413,585 A | 5/1995 | Pagedas | |
| 5,423,821 A | 6/1995 | Pasque | |
| 5,452,523 A | 9/1995 | Jansen | |
| 5,462,542 A | 10/1995 | Alesi, Jr. | |
| 5,483,998 A | 1/1996 | Marelin et al. | |
| 5,488,760 A | 2/1996 | Jansen | |
| 5,560,045 A | 10/1996 | Rockefeller | |
| 5,566,726 A | 10/1996 | Marelin | |
| 5,595,220 A | 1/1997 | Leban et al. | |
| 5,743,310 A | 4/1998 | Moran | |
| 5,755,084 A | 5/1998 | Dekker | |
| 5,766,218 A | 6/1998 | Arnott | |
| 5,797,916 A * | 8/1998 | McDowell | 606/74 |
| 5,832,964 A | 11/1998 | Joshi | |
| 5,850,674 A | 12/1998 | Jansen | |
| 5,972,006 A * | 10/1999 | Sciaino, Jr. | 606/151 |
| 6,014,792 A | 1/2000 | Marelin et al. | |
| 6,030,410 A | 2/2000 | Zurbrugg | |
| D430,781 S | 9/2000 | Hillegonds | |
| 6,200,318 B1 | 3/2001 | Har-Shai et al. | |
| 6,202,706 B1 | 3/2001 | Leban | |
| 6,206,053 B1 | 3/2001 | Hillegonds | |
| 6,260,704 B1 | 7/2001 | Jansen et al. | |
| 6,287,307 B1 | 9/2001 | Abboudi | |
| 6,354,336 B1 | 3/2002 | Leban | |
| 6,481,467 B2 | 11/2002 | Czebatul et al. | |
| 6,516,804 B1 | 2/2003 | Hoffman | |
| D473,773 S | 4/2003 | Hillegonds et al. | |
| 6,705,002 B1 | 3/2004 | Dukes et al. | |
| 6,840,289 B2 | 1/2005 | Hillegonds | |
| 6,854,693 B2 * | 2/2005 | Harrison et al. | 248/68.1 |
| 7,043,315 B2 | 5/2006 | Litao | |
| 7,089,970 B2 | 8/2006 | Bernard | |
| 7,168,331 B1 | 1/2007 | Bernard et al. | |
| 7,299,830 B2 | 11/2007 | Levin et al. | |
| 7,334,610 B2 | 2/2008 | Levin et al. | |
| 7,361,179 B2 | 4/2008 | Rousseau et al. | |
| 7,373,695 B2 | 5/2008 | Caveney et al. | |
| 7,438,094 B2 | 10/2008 | Hillegonds et al. | |
| 7,458,398 B2 | 12/2008 | Hillegonds et al. | |
| 7,484,274 B2 | 2/2009 | Nelson et al. | |
| 7,600,721 B2 | 10/2009 | Vermeer et al. | |
| 7,650,680 B2 | 1/2010 | Stillings et al. | |
| 7,806,895 B2 | 10/2010 | Weier et al. | |
| 2004/0059357 A1 | 3/2004 | Koseki | |
| 2005/0166990 A1 | 8/2005 | Stillings et al. | |
| 2006/0214069 A1 | 9/2006 | Schiebler | |
| 2006/0254031 A1 | 11/2006 | DeMik et al. | |
| 2006/0276809 A1 * | 12/2006 | Oliveira | 606/151 |
| 2007/0021779 A1 | 1/2007 | Garvin et al. | |
| 2007/0055258 A1 | 3/2007 | Hansen | |
| 2007/0056145 A1 | 3/2007 | Stillings et al. | |
| 2007/0290100 A1 | 12/2007 | Caveney | |
| 2009/0078331 A1 | 3/2009 | DeMik | |
| 2009/0078597 A1 | 3/2009 | Abbott et al. | |
| 2009/0114308 A1 | 5/2009 | Marelin et al. | |
| 2009/0121069 A1 | 5/2009 | Dyer et al. | |
| 2009/0242069 A1 | 10/2009 | Segroves | |
| 2009/0271956 A1 | 11/2009 | Nelson et al. | |
| 2010/0139805 A1 | 6/2010 | Sledzinski | |
| 2012/0323241 A1 | 12/2012 | McClellan et al. | |

FOREIGN PATENT DOCUMENTS

| | | |
|---|---|---|
| JP | 2004-113392 | 4/2004 |
| WO | WO 96/04871 A1 | 2/1996 |
| WO | WO 96/41581 A1 | 12/1996 |

OTHER PUBLICATIONS

McClellan et al.; U.S. Appl. No. 12/888,357 entitled "Systems and methods for sternum repair," filed Sep. 22, 2010.

* cited by examiner

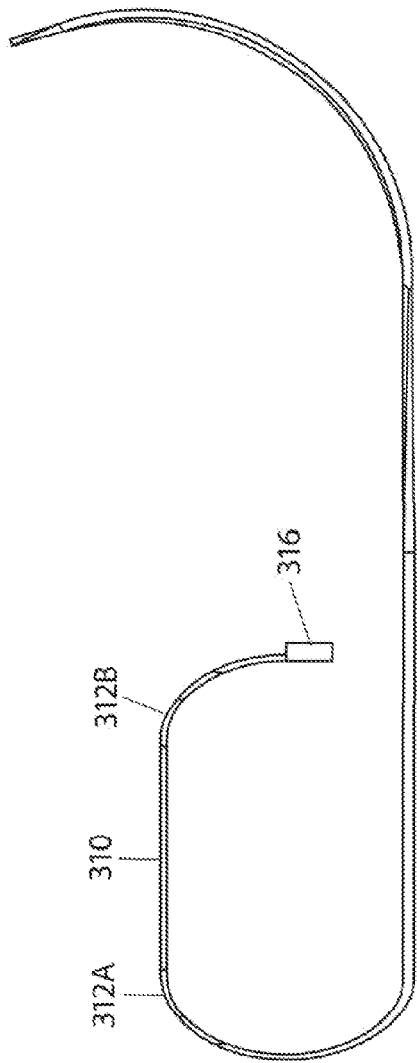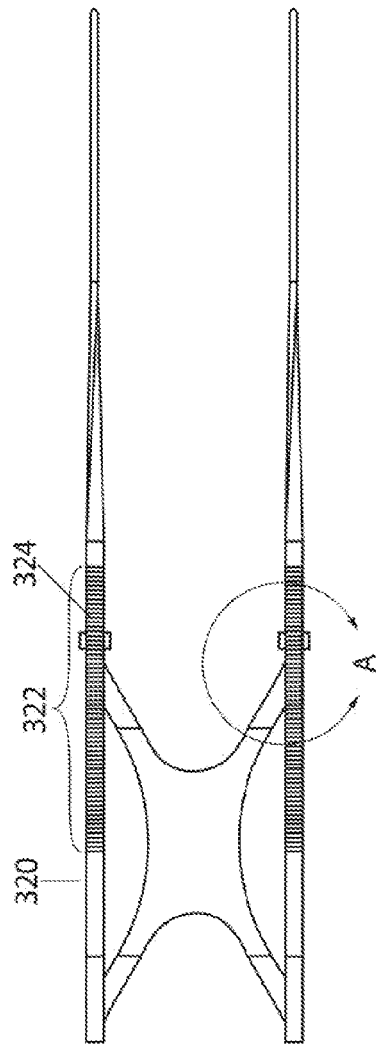

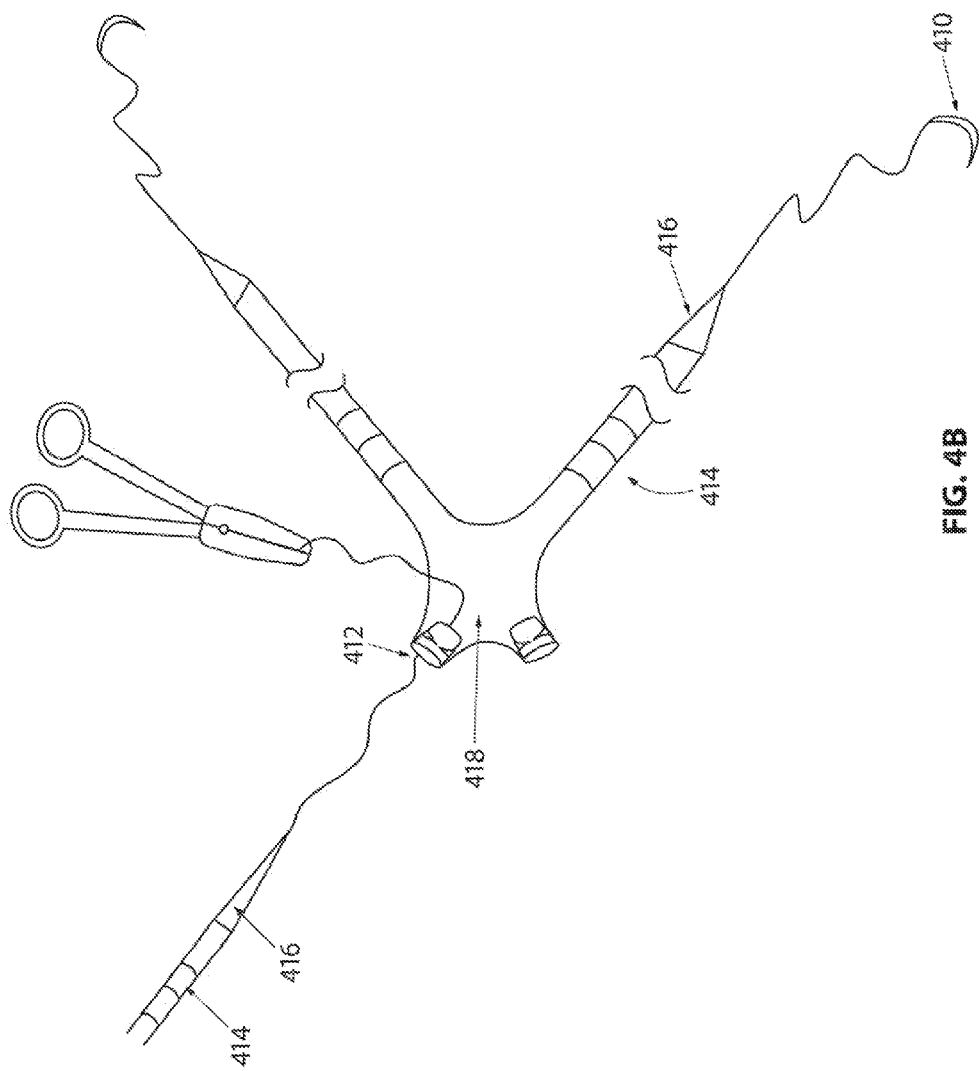

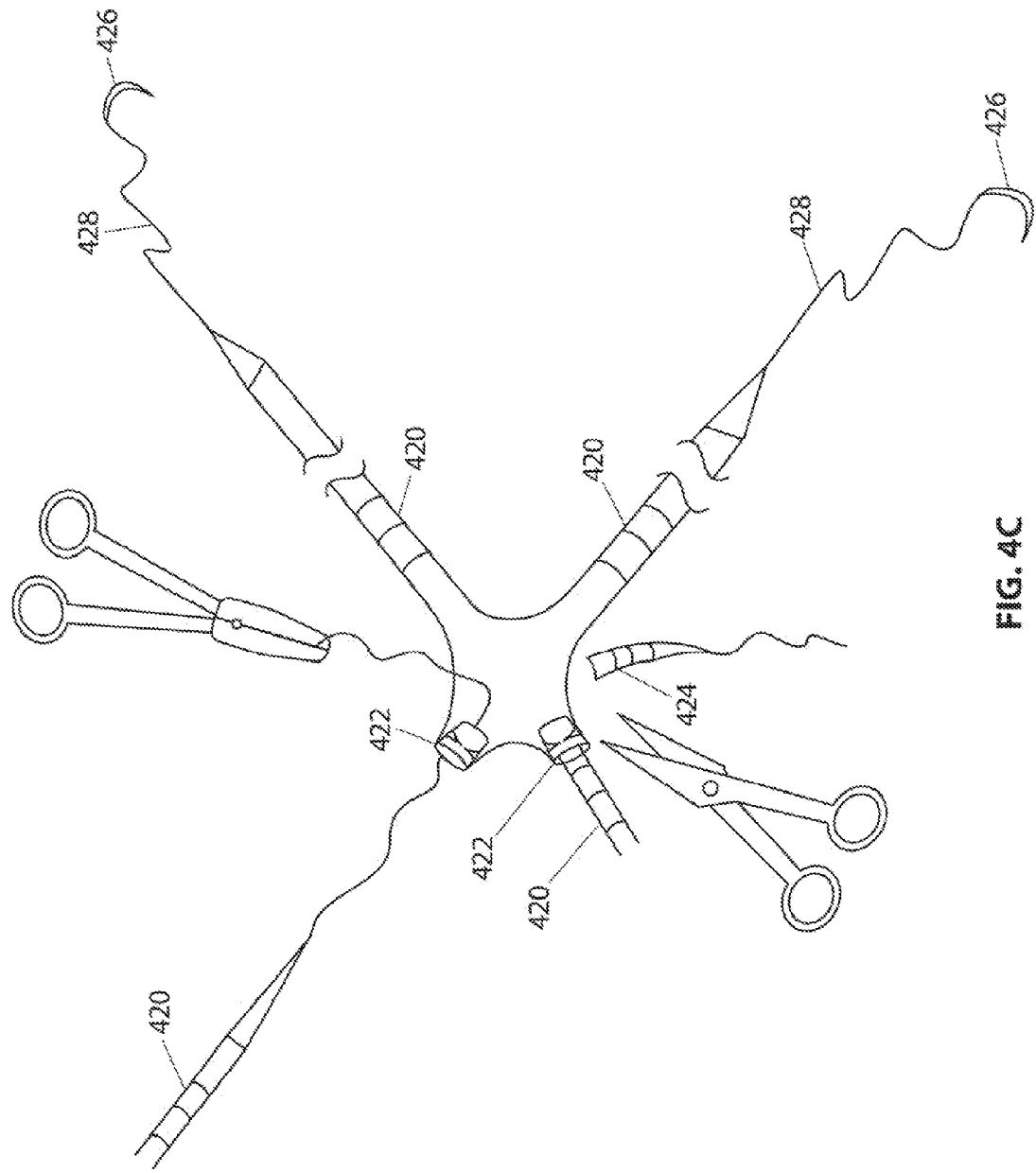

SYSTEMS AND METHODS FOR STERNUM REPAIR

CROSS-REFERENCE

This application claims the benefit of U.S. Provisional Application No. 61/161,515 filed Mar. 19, 2009 and U.S. Provisional Application No. 61/252,145 filed Oct. 15, 2009, which applications are incorporated herein by reference in their entirety.

BACKGROUND OF THE INVENTION

Conventional methods for sternum repair following surgery often involve extensive forces being applied, which may be difficult to apply and uncomfortable. For example, sternal repair following heart surgery typically uses steel wire which is passed between the ribs and twisted/crimped together to achieve stability between the bone edges.

For sternal reconstruction the wires are subject to stress forces caused by sternal movement from breathing. This leads to metal fatigue and fracturing. Wire integrity loss can cause sternal infection and non-union. This occurs in 5% of all open heart surgeries. Furthermore there have been reports of allergy to metals which often prompts the removal of wires and risk exposure by the patient. The wires are also dependent upon the skill of the surgeons as they tighten the wires. Too many turns in the wire may unnecessarily weaken the wire and subject it to future failure. Sternal plating systems have been developed, much like plates for fractured bones; however there are many hurtles in the success of the plates. They are cumbersome and difficult to apply, and the cardiothoracic surgeons are usually not trained or comfortable with the application. Typically, they are reserved for sternal dehiscence cases, and they are expensive.

Accordingly, there exists a need for improved systems and methods for sternum repair.

SUMMARY OF THE INVENTION

The invention provides systems and methods for sternum repair. Various aspects of the invention described herein may be applied to any of the particular applications set forth below or for any other types of tissue connection. The invention may be applied as a standalone system or method, or as part of integrated medical procedure, such as cardiac surgery. It shall be understood that different aspects of the invention can be appreciated individually, collectively, or in combination with each other.

One aspect of the invention is directed to a sternum connecting device. The sternum connecting device may include a central body. The central body may include a plurality of male stems, a plurality of male bases connected to the male stems, a plurality of female stems, and a plurality of female bases connected to the female stems. The sternum connecting device may also include a plurality of male sutures, wherein a male suture extends from a male base and is configured to be revised female base, wherein at least one of the male stems or female stems is oriented at a non-parallel angle to another male stem or female stem.

In accordance with another embodiment of the invention, a connection device may be provided comprising a central body. The central body may include a plurality of male stems, a plurality of male bases connected to the male stems where a male base is configured to serve as a taking off point of a male suture, a plurality of female stems, and a plurality of female bases connected to the female stems where a female base is configured to accept the male suture taking off from the male base. In some instances, at least one of the male or female bases may be configured to enable the male suture to change orientation at the male or female base with respect to the male or female stem to which the male or female base is connected.

A method for connecting two tissues may be provided in accordance with another aspect of the invention. The method may include a step of providing a connection device, which may include a central body with a plurality of male stems, a plurality of female stems, and a plurality of female bases connected to the female stems. The connection device may also include a plurality of male sutures, wherein a male suture may be connected to and extend from a male stem. The method may also include the steps of wrapping a first male suture around the two tissues and connecting the first male suture to a first female base, and wrapping a second male suture around the two tissues and connecting the second male suture to a second female base.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3B shows a side view of another embodiment of a sternal device.

FIG. 3C shows a bottom view of another embodiment of a sternal device.

FIG. 4B shows a sternum connecting device after a needle is drawn through a female base.

FIG. 4C shows a sternum connecting device as a male suture is drawn through a female base.

DETAILED DESCRIPTION OF THE INVENTION

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Sternal Device

Figure 1:
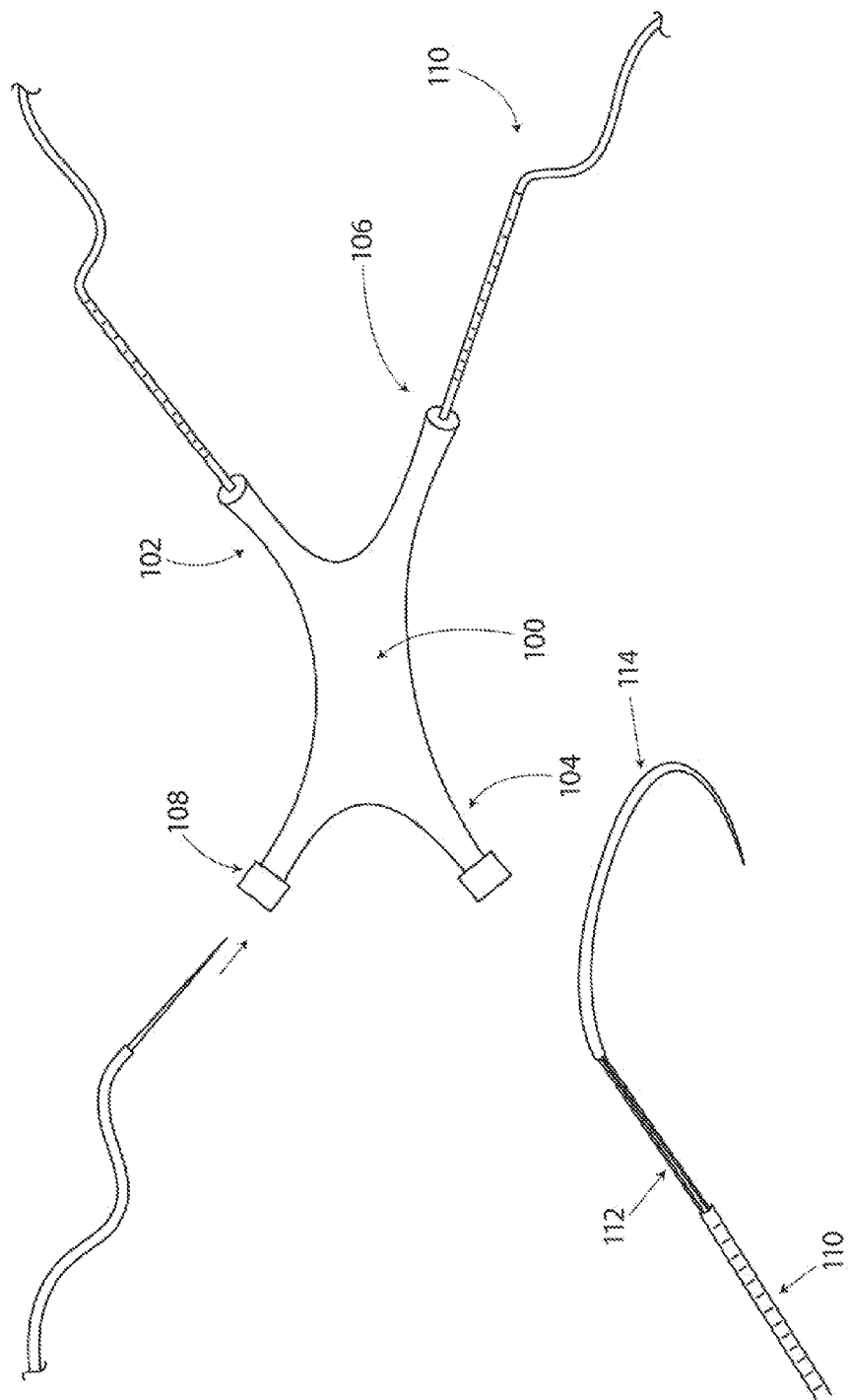
FIG. 1 shows a sternal device in accordance with an embodiment of the invention.

FIG. 1 shows a sternal device in accordance with an embodiment of the invention. A sternal device may include a central body 100 which may include one, two, or more male stems 102 and one, two, or more female stems 104. Preferably, the central body has a plurality of male stems and a plurality of female stems. A central body may also optionally include one, two, or more male bases 106 and one, two, or more female bases 108.

Any number of male stems, female stems, and/or corresponding bases may be provided. Preferably, the same number of male and female stems may be provided. For instance, if two male stems are provided, two female stems are provided. Alternatively, there may be different number of male and female stems. In some examples, one, two, three, four, five, six, seven, eight, or more male stems, female stems, and/or corresponding bases may be provided (e.g., two male stems and one female stem).

The male and/or female stems may be integral to the central body. Alternatively, they may be separable from the central body. This will be discussed in further detail below.

A male base may be connected to a male stem, and female base may be connected to a female stem. In preferable embodiments, each male base may be connected to a male stem, and each female base may be connected to a female stem. Alternatively, a plurality of male bases may be connected to a male stem and/or a plurality of female bases may be connected to a female stem. In other embodiments, a plurality of male stems may be connected to a male base and/or a plurality of female stems may be connected to a female base. In some embodiments, a male stem does not have a male base, or a female stem does not have a female base.

In some embodiments, a male stem and/or female stem may have an elongated shape. The degree of elongation may vary (e.g., male and/or female stems may be long and thin, or more short and stubby). Male and/or female stems may extend from a common central region of the central body. At least one male stem or female stem may be oriented at a non-parallel angle to another male stem or female stem. In some instances, all male stems may form non-parallel angles with respect to other male stems and/or all female stems may form non-parallel angles with respect to other female stems. The male and/or female stems may all intersect from the common central region of the central body. Alternatively, some male and/or female stems may intersect at or near a common central region of the central body. In some instances, the male and female stems may form a cross-shape or X-shape. Alternatively, they may form a shape similar to spokes on a wheel, extending from a common central region.

A sternal device may also include one or more male sutures 110. A male suture may extend from a male base. The male stem may be integral or separable from the male base. Alternatively, a male suture may be integral or separable from a male stem and extend from the male stem. Preferably, each male base may be connected to a male suture. Preferably a one-to-one correspondence may exist between a male stem and a male suture. Alternatively, male stem may be directly or indirectly connected to zero, one, two, or more male sutures. Or a male suture may be directly or indirectly connected to one, two, or more male stems.

A male suture 110 may be configured to be received by a female base 108. Preferably, each male suture may be configured to be received by a different female base. Each male stem may have a corresponding female stem, which may be connected via a male suture. Alternatively, a female base may be configured to receive a plurality of male sutures. In some embodiments, a female base may receive a male suture so that the male suture may only travel in one direction with respect to the female base. For example, a male suture may pass through the female base in only one direction. This may result in tightening the sternal device without allowing it to be loosened. Alternatively, a tightening mechanism may be provided on the female base. For example, a male suture may be allowed to slide in either direction through a female base until the tightening mechanism is engaged, and the male suture is fixed in place, or only allowed to slide in one direction with respect to the female base.

The bases may serve as the "take off" and "receptacle" of a male suture. The male base may be where the security of the male-female interaction is.

In some instances, a male suture 110 may have an engagement zone 112. A male suture may have a first end and an opposing second end. The first end of the male suture may be at a male base or male stem from which the male suture extends. The engagement zone may be at the second end of the male suture. The engagement zone may narrow the male suture. For example, if a male suture has a diameter D1 along its length, at the engagement zone, the diameter of the male suture may decrease to D2, where D2 is less than D1. The diameter decrease may occur gradually or suddenly. Similarly, if a male suture has a width W1 along its length, at the engagement zone, the width of the male suture may decrease to W2, where W2 is less than W1. The width decrease may occur gradually or suddenly. In some instances, an engagement zone may have a conical or tapered shape. The engagement zone may be a cone-like dilator or can be a standard suture.

A male suture 110 may optionally be connected to a delivery needle 114. The delivery needle may or may not be directly connected to an engagement zone 112 of a male suture. In some instances, the delivery needle may be indirectly connected to an engagement zone of the male suture via a line or thread. Alternatively, the delivery needle may be directly or indirectly connected to the male suture without going through an engagement zone. In some instances, the delivery needle may be separable from the male suture or may be integral to the male suture. In some instances, an engagement zone of the male suture may be formed of a pointed and rigid material that may be used as a delivery needle. The delivery needle may be substantially straight or may be curved. The delivery needle may be any needle known or later developed in the art which may allow the delivery of the sternal device around the sternum.

A sternal device may be delivered around a sternum or other similar anatomical features to connect pieces of the sternum. A sternal/rib horizon may be where the sternum and rib may meet. There may be soft tissue above and below where a male suture may pass through. Application of a sternal device within a subject will be discussed in further detail below.

Figure 2:
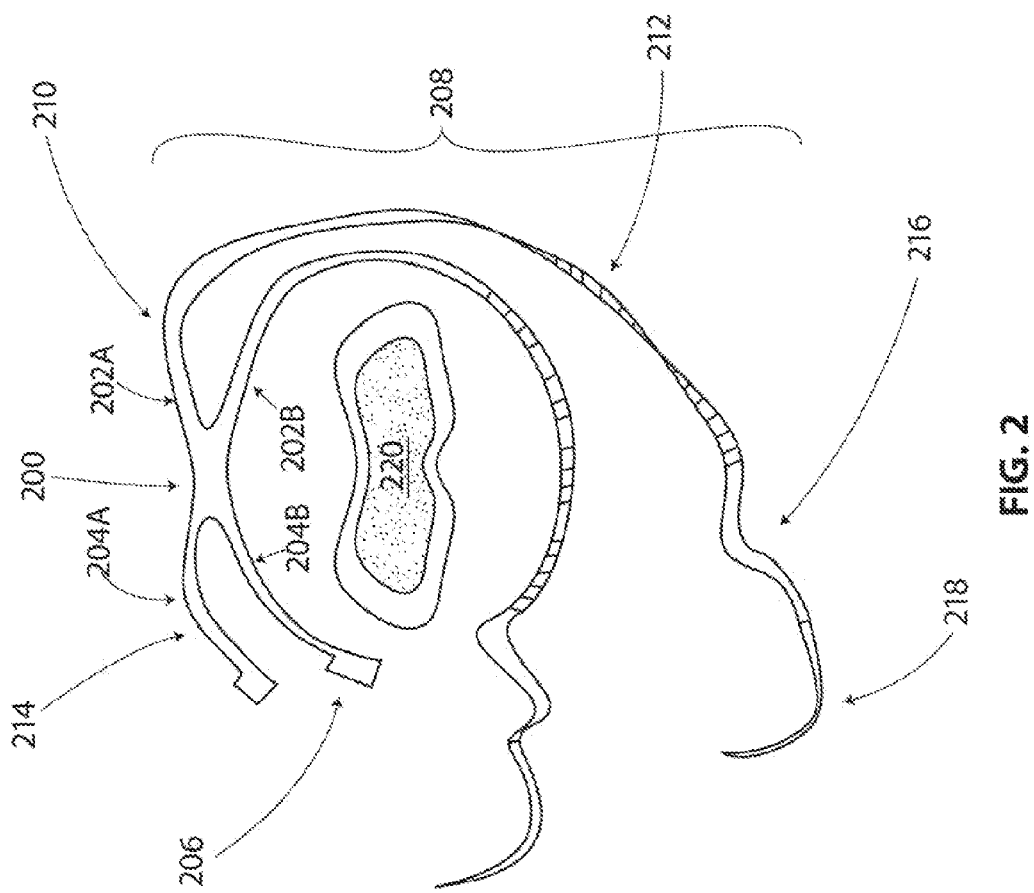
FIG. 2 shows another configuration for a sternal device.

In some embodiments, a male suture is configured to be accepted by a female base that is not adjacent to the male base from which it extends. For example, if a sternal device has a pair of female stems with corresponding female bases, and a pair of male stems with corresponding male bases, a first male suture from a first male base may be accepted by a first female base, where the first male base and first female base are on stems that are not adjacent to one another, but rather are opposite one another. Similarly, a second male suture from a second male base may be accepted by a second female base, where the second male base and second female base are on stems that are not adjacent to one another, but rather are opposite one another. In such situations, the first male suture may be configured to cross the second male suture when the first and second male sutures are received by their respective female base. Thus a first male suture may cross over a second male suture, or vice versa, when they are accepted by their respective female bases. Thus, a first male suture may contact and/or intersect a second male suture FIG. 2 shows another configuration for a sternal device. The sternal device may have a main body 200. The main body may have a plurality of elongated stems. For example, two male stems 202a, 202b and two female stems 204a, 204b may be provided. In some instances, the male and/or female stems may be long and narrow. A female stem may be connected to a female locking zone 206. The female stem may be the base 214 of the female suture. The female locking zone may be configured to accept a male suture 208.

In some embodiments, the main body, female stem, and/or male stems may be made of a rigid, semi-rigid, or flexible material. A male suture may preferably be made of a flexible material, although alternatively it may be made of a semi-rigid or rigid material. Any of the components may be made from the same or different materials with various material properties. Any of the materials may or may not extend, stretch, bend, fold, or retain shape.

A male suture 208 may extend from a male stem 202a. In some instances, the male suture may be integral to the male stem. The male stem may be the base 210 of the male suture. The male suture may be narrower than the male stem. Alternatively, the male suture may have a similar cross-sectional size to the male stem. The male suture may gradually decrease in cross-sectional area as it extends from the male stem. Alternatively, it may retain the same cross-sectional area. In some instances, the male suture may be more flexible than the male stem.

A male suture 208 may include a male locking zone 212. The male locking zone may include locking features that may be accepted by a female base 214, but may prevent the male suture from sliding in at least one direction with respect to the female locking zone 206. For example, the male suture may pass in one way through the female base to tighten the sternal device, but may be prevented from passing in the opposite direction through the female locking zone. The male locking zone may be provided along the entire length of the male suture. Alternatively, it may be along one or more portions of the male suture. The locking zone may be closer to the end of the suture adjacent to the male stem, or may be closer to the end of the suture that is received by the female locking zone.

The locking features provided on a male locking zone may include any suture morphology or structure that may assist with causing the male suture to lock within the female locking zone, to prevent the male suture from moving in at least one direction. The locking zones may include ball shapes, cone shapes, bumps, teeth, jagged edges, holes, or grooves.

The male suture 208 may have an engagement zone 216. The engagement zone may narrow the male suture. The engagement zone may have orientation features. An engagement zone may assist with guiding a male suture through a female locking zone. In some embodiments, the engagement zone may be adjacent to a locking zone. Alternatively, the engagement zone may be adjacent to a region of the male suture that is not the male locking zone.

The male suture 208 may optionally be connected to a delivery needle 218. The delivery needle may or may not be directly connected to an engagement zone 216 of a male suture. The delivery needle may be any needle known or later developed in the art which may allow the delivery of the sternal device around the sternum.

The sternal device may be configured to wrap around a sternum. A cross-section a sternum may be illustrated 220. A main body may be disposed along a first side of a sternum, while the male sutures may wrap around the opposing side of the sternum. A male suture may engage with the female locking zone, so that the male locking zone contacts the female locking zone. The sternum may be encircled by the sternal device.

Figure 3A:
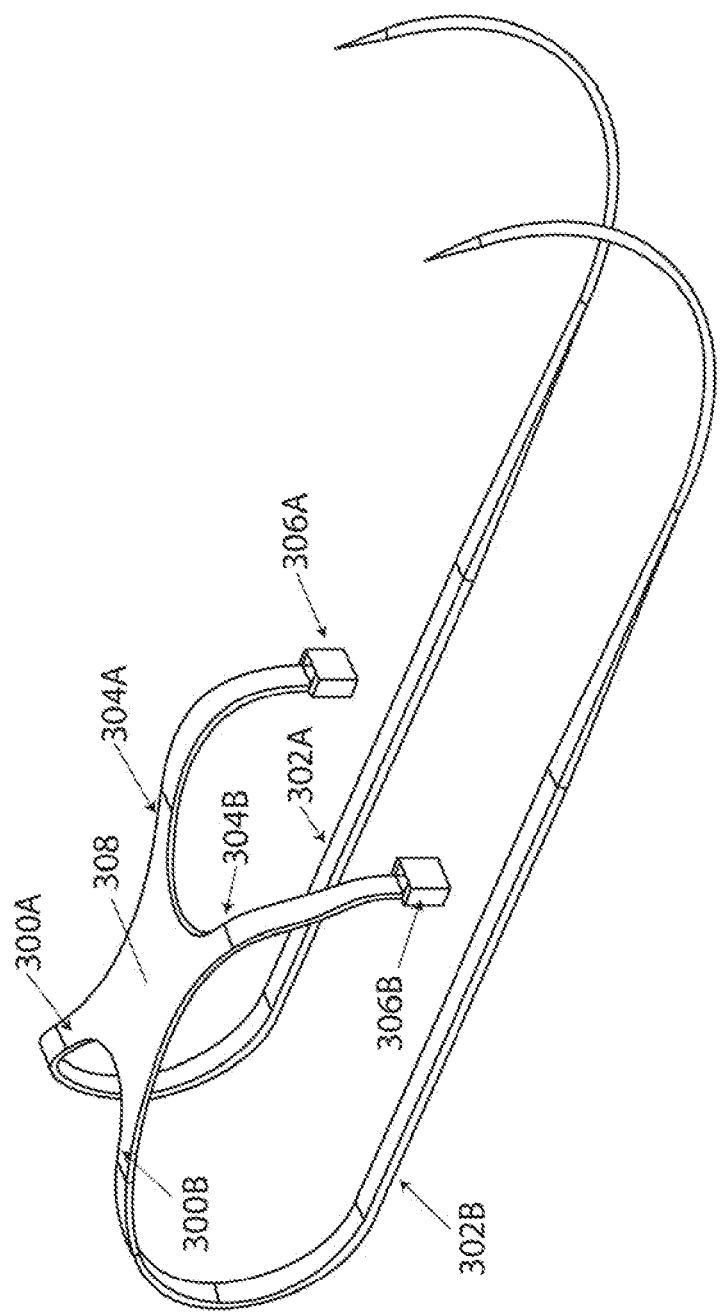
FIG. 3A shows an upper perspective view of another embodiment of a sternal device.

FIG. 3A shows an upper perspective view of another embodiment of a sternal device. The sternal device may include two male stems 300a, 300b connected to male sutures 302a, 302b and two female stems 304a, 304b connected to two female locking zones 306a, 306b. The male stems and the female stems may be oriented within the main body 308 so that the male stems are not parallel to one another and the female stems are not parallel to one another. The male and female stems may be oriented to form a cross-shape.

Male sutures may be integrally connected to the male stems. The male sutures may be provided of a flexible, semi-rigid, or rigid material. In some instances, a male suture 302a may engage with a female stem 304a that is adjacent to the corresponding male stem 300a of the male suture. In such situations, when the male sutures engage with their corresponding female locking zones, the male sutures may be substantially parallel to one another. The male sutures are not intersecting one another. In other instances, a male suture 302a may engage with a female stem 304b that is not adjacent to the corresponding male stem 300a of the male suture, but is opposite the corresponding male stem. In such situations, when the male sutures engage with their corresponding female locking zones, the male sutures may be substantially non-parallel to one another. The male sutures are intersecting one another, and may form a cross-shape.

The central portion of the main body may be substantially flat and may fit over a first side (front) of a sternum. The male and/or female stems may be contoured to wrap around a sternum so that they hang over the sides of the sternum. Thus, a male suture may engage with a female locking zone over a side of a sternum rather than over the front side of a sternum. Similarly, a male suture may connect to a male stem over a side of the sternum rather than over the front side of the sternum.

In alternate embodiments, the length and/or contour of the male and female stems may vary. Thus, in some alternate embodiments the male suture and female locking zone may interface along the front side of the sternum adjacent to the central part of the main body, or along the back side of the sternum, or anywhere along the circumference of the sternum.

FIG. 3B shows a side view of another embodiment of a sternal device. The profile of the sternal may be thin, so that there aren't significant bumps or protrusions from the sternal device when it is used within a subject. For example, the central part of the main body 310, the stems of the main body 312a, 312b, the male sutures 314, the female locking zones 316, and/or any other components may have a very low profile, and may be shaped to fit a sternum (or other comparable anatomical region) of the subject.

In some embodiments, the components of the sternal device may be 1 cm or less in profile, or may be about 0.5 cm or less, 0.3 cm or less, 0.2 cm or less, 0.1 cm or less, 0.07 cm or less, 0.05 cm or less, 0.02 cm or less, 0.01 cm or less, 0.007 cm or less, 0.005 cm or less, 0.002 cm or less, 0.001 cm or less. The contours of the sternal device may also be smooth so that no rough or sharp edges are protruding from the sternal device. This may help prevent the sternal device from causing irritation or getting caught on tissues within the region.

In some embodiments, the interface where a male suture extends from a male stem may be smooth. The male suture may be integrally connected to the male stem. Alternatively, the male suture may be separable from the male stem and/or may be connected via a male base. The profile where the male base connects to the male stem and/or base may still be very thin and/or smoothly contoured.

FIG. 3C shows a bottom view of another embodiment of a sternal device. The male suture 320 may include a male locking zone 322 that may include locking features 324. In some embodiments, the locking features may be on the bottom side of the sternal device. For example, the locking features may include ball shapes, cone shapes, bumps, teeth, jagged edges, holes, or grooves. The male locking zone may be long at least part of the length of the male suture where the male suture is likely to engage with the female locking zone.

Figure 3D:
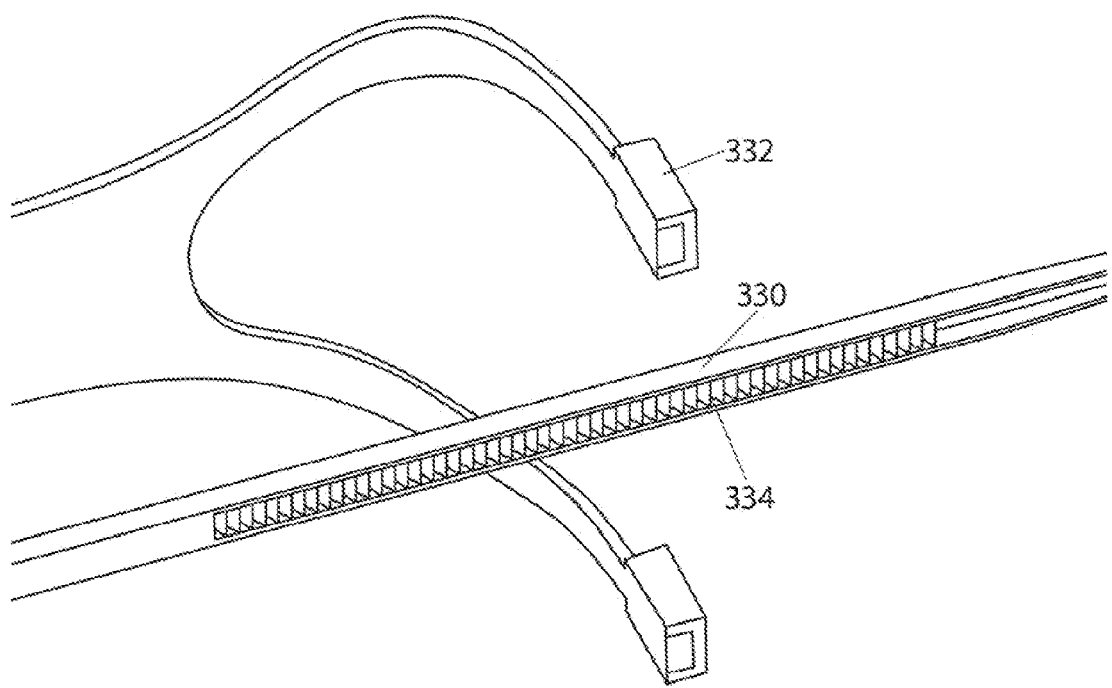
FIG. 3D shows a lower perspective view of another embodiment of a sternal device.

FIG. 3D shows a lower perspective view of another embodiment of a sternal device. A close up is provided of a male locking zone 330 from the bottom of the sternal device. A close up is also provided of a female locking zone 332. The male locking zone may be guided into the female locking zone via the end of the male suture. The end of the male suture may optionally include a delivery needle and/or engagement zone.

The male locking zone may include locking features such as ridges 334. The locking features may be shaped so that the male suture may pass more easily in one direction through the female locking zone than in the other direction. The female locking zones may or may not include corresponding locking features within. In some instances, the female locking zone may have an outer surface and an inner surface. The inner surface may contact the male suture. The inner surface may comprise locking features that may correspond to the locking features of the male suture and prevent or make it difficult for the male suture to move in at least one direction with respect to the female locking zone. The female locking features may also be ridges, bumps, balls, grooves, hooks, bars, ratchets or anything similar.

Figure 4A:
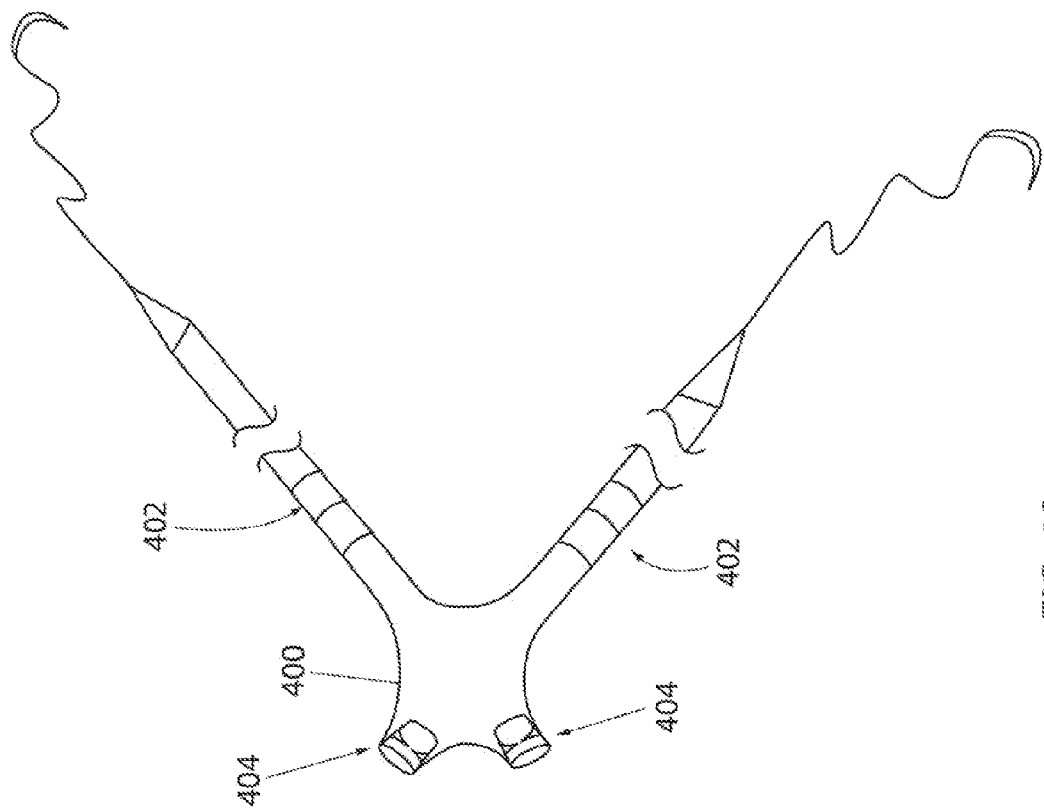
FIG. 4A shows a sternum connecting device in accordance with an embodiment of the invention.

FIG. 4A shows a sternum connecting device in accordance with an embodiment of the invention. The sternum connecting device may include a central structure 400, a plurality of elongate members 402, and a plurality of lock devices 404. For example, a central structure may be connected to two elongate members that may extend from the central structure. Two lock devices may be connected to the central structure.

In some embodiments, the elongate members may extend from one side of a central structure while the lock devices may be provided on a second opposing side of the central structure. For example, if elongate members extend from a right side of a central structure, the lock device may be provided on the left side of the central structure. Thus, the elongate members may be adjacent to one another, while the lock devices may be adjacent to one another. In other embodiments, the elongate members and/or lock devices need not extend from the same side. For example an elongate member may extend from a right upper corner of a central structure, a lock device may be positioned on a right lower corner of the central structure, an elongate member extend from a lower left corner of the central structure, and a lock device may be positioned at the upper left corner of the central structure. In such situations, the elongate members are not adjacent to one another and the lock devices are not adjacent to one another.

In some embodiments, the take-off and degree of the male elongate members may be adjustable. This may allow the sternum connecting device to be placed in an optimal manner in relation to the ribs.

The female lock devices may be on an anterior or posterior surface of the central device. Alternatively, they may be provided on the side of the central device. The female lock devices may be fixed relative to the central structure, or may be pivotally connected to the central structure (e.g., by a pin). The female lock device can be attached to the central structure via the central pin which may allow it to rotate to an optimal angle to accept the male elongate member. The female lock device may be shaped to accept a flat or round male elongate member. The various profiles and shapes of the male elongate members may be discussed in greater detail below. The female lock devices may be built into the central structure to be as smooth and low profile as possible.

The sternum connecting device may be low profile and simple. In some instances, the central structure may be as flat as possible (low profile).

The sternum connecting device may utilize some of the similar principles to traditional wire placement techniques. The sternum connecting device may allow for quick application, and may be easily cut in an emergency. Furthermore, the sternum connecting device does not need drills, screws, or plates.

In some instances, the sternum connecting device may have a potential for resorption. The sternum connecting device and/or any of its components may be formed of a material that may be reabsorbed within the body. The sternum connecting device and/or any of its components may include an antibiotic coating or growth factor coating. Materials associated with the sternum connecting device may be discussed in greater detail below.

FIG. 4B shows a sternum connecting device after a needle 410 is drawn through a female locking device 412. The needle may be connected to a male elongate member 414. The needle may be directly connected to the male elongate member or may be indirectly connected to the male elongate member via a thread or line. The male elongate member may also have an engagement zone 416 that may have a conical or tapered shape that may assist with guiding the male elongate member through the locking device. In some embodiments, the engagement zone may provide the same function as the needle. In some instances, the engagement zone may be pointed, and may enable a user to thread the male elongate member through soft tissue via the pointed engagement zone.

A central member 418 of the sternum connecting device may be placed proximate a sternum, wrapping a first one of the elongate members around the sternum, and inserting it (e.g., via the needle and thread) through a first one of the locking devices such that it engages with the first locking device. The second elongate member can be wrapped around the sternum, inserted through the second locking device, such that it engages the second locking device. The delivery end of each elongate member can be cut off after insertion through the locking device, e.g., to make the elongate member flush with the locking device. For instance, a needle is cut off and the thread/elongate member pulled through the female locking device. Or the elongate member may be directly pushed or pulled through. In this manner, the apparatus may form a more robust sternal fixator that counteracts the various forces that are experienced between the cut pieces of the sternum following a sternotomy.

The central core structure can have relaxing cuts in it to allow the female locking devices some wiggle or bend. This may provide breathing room that may take some stress off the sternum connecting device.

FIG. 4C shows a sternum connecting device as a male elongate member 420 is drawn through a female locking device 422. A first elongate member has already been inserted into a female locking device and the excess elongate member 424 cut off.

A needle 426 may be passed behind a rib and sternum. The needle may be a standard needle driver, such as in a standard wire, or any needle known or later developed in the art. The needle may be connected to a line 428, which may connect it to an elongate member. The needle may be cut off and the thread and/or elongate member may be pulled through a female locking device.

Once engaged through the female, the excess male elongate member may be cut off and discarded. A cutting device may also be used to tighten to device to any appropriate force level desired.

Central Body

Figure 5:
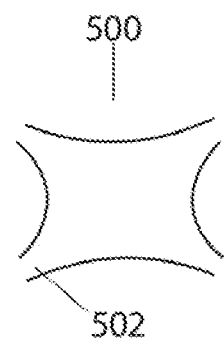
FIG. 5 shows an example of a central body shape.

FIG. 5 shows an example of a central body shape 500. A central body may include a plurality of stems 502 that may extend from a central region of the central body. In some instances, the central body may be symmetrical about a central vertical axis and/or a central horizontal axis. Any number of stems may extend from a central body. For example, two, three, four, five, six, eight, ten, twelve, or more stems may extend from the central body. The stems may extend so that they are substantially evenly spaced out, or they may be spaced so that some are closer to others, or that they are arranged in groups.

The stems may have any shape or dimensions. In some instances, the stems may be long and narrow, while in other instances they may be short and stubby. In some instances, the stems may barely protrude from the central region of the central body. In some instances, a central region of the central body may be larger while in other instances the central region. In some embodiments, the central body may have a curved contoured shape, while in other embodiments, the central body may have more abrupt or angular shapes.

Preferably, the stems may be integral to the central body. Alternatively, one or more stems may be separable from the rest of the central body. In some instances, one or more stem may connect to another stem, or may connect to a central region of the central body.

Figure 6:
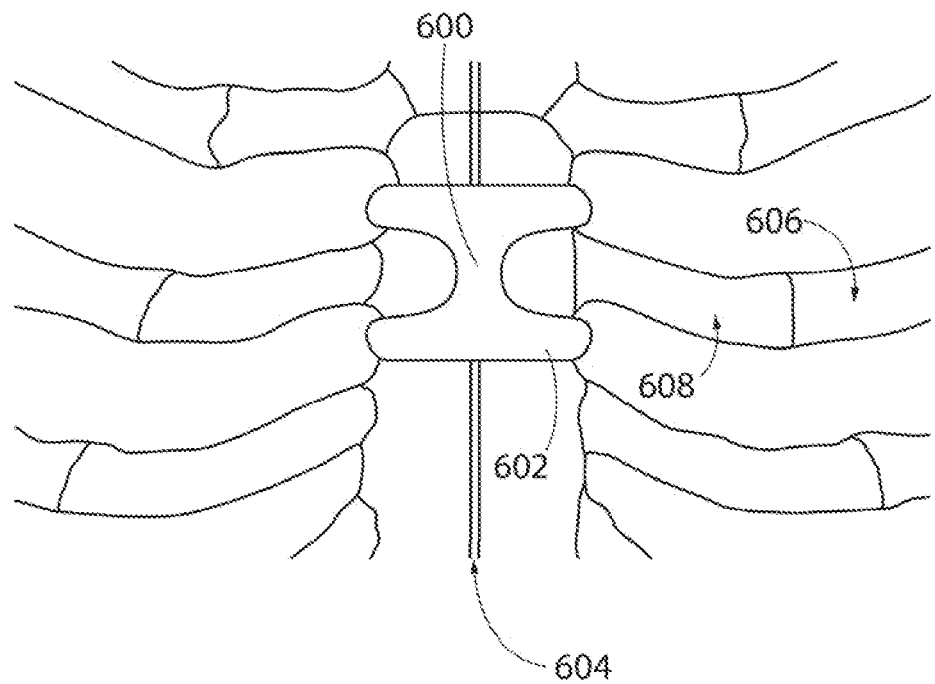
FIG. 6 shows another example of a central body shape.

FIG. 6 shows another example of a central body shape. In some embodiments, the central region 600 of the central body may be elongated so that the central body with the stems forms more of an "H" or "I" shape. In some instances, the stems 602 may be parallel or substantially parallel to one another. Alternatively, the stems may be substantially non-parallel to one another. The shape of the stems may be provided so that parts of the stem are not parallel to one another, while other parts are not. In some instances, the stems may be substantially straight, while in other instances they may be curved or bent. The stems may intersect one another or may intersect a central region of the central body.

The central body may be placed on a sternum so that the central body spans the midline 604 of the sternum. The stems of the central body may be positioned between one or more ribs 606, and the associated costal cartilages 608. The stems may wrap around to at least a portion of the sides of the sternum.

Figure 7A:
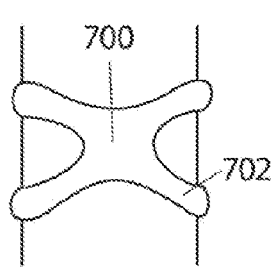
FIG. 7A shows a central body with elongated stems.

FIG. 7A shows a central body 700 with elongated stems 702. The stems may form an 'X' shape. In some embodiments, the stems may narrow as they extend from a central region of the central body. Alternatively, they may retain the same width and/or get wider as they extend from the central region of the central body. The central body may be a substantially planar or curved planar body, as opposed to two or more overlapping planes or layers.

Figure 7B:
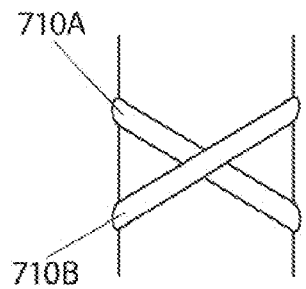
FIG. 7B shows a central body with multiple layers.

In some instances, the stems may wrap around at least a portion of a side of the sternum FIG. 7B shows a central body with multiple layers 710a, 710b. In some instances, a central body may include stems that may form a cross shape as two elongated stem pairs may cross over one another. However, even if stem pairs cross over one another, they may retain a low profile. Thus, in some embodiments, a central body may have two or more overlapping planes or layers. In other embodiments, preferably, a central body may only have one layer.

Figure 7C:
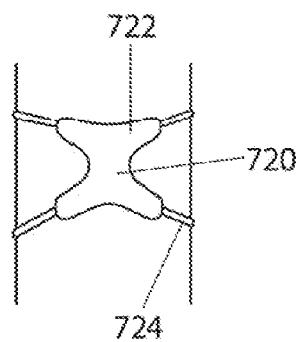
FIG. 7C shows a central body with shorter stems.

FIG. 7C shows a central body 720 with shorter stems 722. In some instances, the central body may be sized so that the stems do not wrap around a side of the sternum, but may be entirely on a front or back (anterior or posterior) side of a sternum. A central body may have any shape, which may include an 'X' shape, 'H' shape, 'I' shape, 'T' shape, 'K' shape, or ')('shape. One or more suture 724 may wrap around the sternum.

The central body may have any size. The central body may be roughly sized to fit a sternum. In some instances, the footprint of a central body may be on the order of W by H, where W represents a width dimension and H represents a height dimension. The values for W and/or H may be on the order of about 10 cm or less, 8 cm or less, 3 cm or less, 5 cm or less, 4 cm or less, 3.5 cm or less, 3 cm or less, 2.5 cm or less, 2 cm or less, 1.5 cm or less, or 1 cm or less. W and H may have about the same dimensions, or may have differing dimensions. In some instances, a central body size may be selected to fit a sternum. In other embodiments, a body may be provided for a sternum, and aspects or components of the size may be variable in order to be made to fit the sternum.

Figure 8:
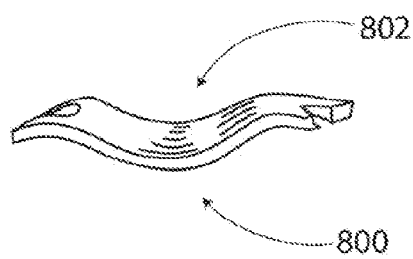
FIG. 8 shows a contoured central body of a sternal device.

FIG. 8 shows a contoured central body of a sternal device. In some embodiments, a central body may have a low profile. The central body may be contoured to fit the contour of a sternum. In some embodiments, a sternum may include a convex region, and the central body may include a corresponding convex region. In other embodiments, the sternum may include a concave region and the central body may include a corresponding concave region. In some instances the sternum may have a curved planar configuration. Thus, the central body may retain a low profile and conform as much as possible to the shape of the sternum. By being low profile, the sternal may be not as palpable by a subject post operation. One surface may correspond to the deep surface/posterior 800 side and the other surface may correspond to the superficial/anterior 802 side In some embodiments, different central body sizes and/or configurations may be provided to fit different sternums. For example, a different central body size and/or profile may be provided for a child as opposed to an adult. A central body size may be selected to accommodate the subject.

In alternate embodiments, the central body may be relatively flat. In such situations, the central body may provide a flat surface around the sternum. Thus, in some instances, the central body may have a substantially planar configuration. The central body may have an elongated shape.

In some instances, the material for the central body may be selected to assist with conforming to a sternum shape. The central body may be designed to minimize or reduce lift off the sternum. For example, the central body may be formed of a flexible material and/or have flexible components that may allow it to conform to the shape of a sternum. In other embodiments, the central body may be rigid or semi-rigid, or may have rigid or semi-rigid features that may allow it to maintain a desired profile.

Figure 9:
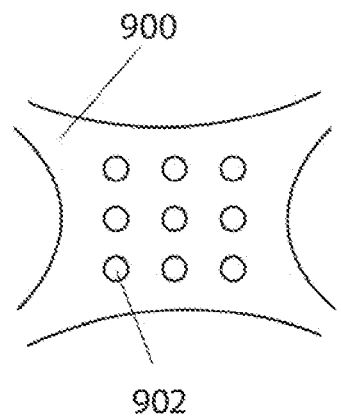
FIG. 9 shows a central body of a sternal device with holes.

FIG. 9 shows a central body 900 of a sternal device with one or more holes 902. In some instances, the central body may have holes that may enable underlying bone tissue and/or soft tissue to grow in through the holes and/or develop through the holes. This may assist with anchoring the central body into place. Better incorporation of the device onto the underlying tissue may cause the device to be stronger.

A plurality of holes may be provided. In some instances, the holes may be provided as an array, or in rows or columns, or with a concentric or staggered pattern. Alternatively, the holes may have any placement. In some instances, the holes may have any diameters, including holes on the order of 2 cm diameters, 1 cm diameters, 0.75 cm diameters, 0.5 cm diameters, 0.3 cm diameters, 0.2 cm diameters, 0.1 cm diameters, 0.05 cm diameters, or 0.01 cm diameters. The holes may have the same or different diameters.

Figure 10:
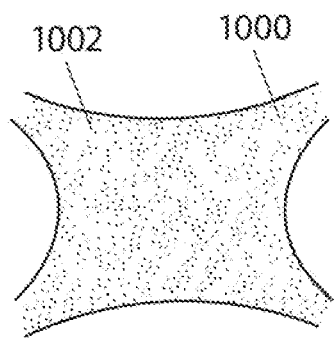
FIG. 10 shows a central body of a sternal device with an irregular textured surface.

FIG. 10 shows a central body 1000 of a sternal device with an irregular textured surface 1002. The irregular textured surface may include surface roughness, bumps, ridges, grooves, pits, or any other surface feature that may provide texture to the surface. In some instances, the central body of the sternal device may have microscopic undulations or other textured surface features. Providing an irregular textured surface may enable a bodily tissue, such as underlying bone tissue, and/or soft tissue to grow into the surface irregularities. This may also assist with anchoring the central body into place. Providing a bumpy bone interface may give the sternum or other underlying anatomical feature something to grab ahold of, and assist with forming a fibrous bond.

In some embodiments, additional anchors may be provided to keep a central body in place with respect to the sternum, or any other underlying anatomical structure. For example, drills, screws or similar features may be used to anchor the central body.

Figure 11:
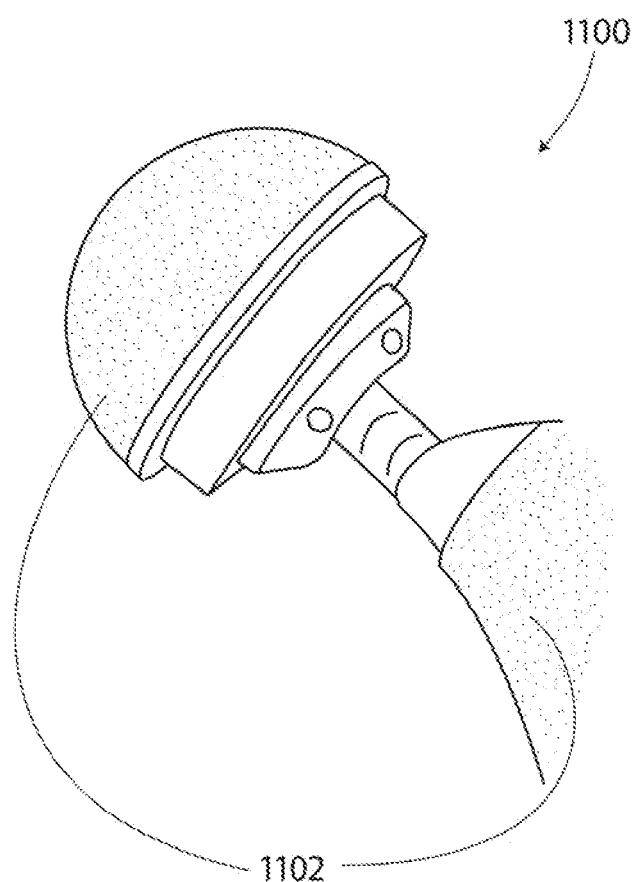
FIG. 11 shows an artificial hip joint with an irregular textured surface.

FIG. 11 shows an artificial hip joint 1100 with an irregular textured surface 1102. The irregular textured surface may encourage a subject's body part to grow into the textured surface. These irregularities may be similar to the irregularities that may be provided on a central body of a sternal device.

The sternal device may be fitted to follow closely with a sternum shape, or the shape of any other underlying anatomical feature. By fitting the device to the sternum, the mechanical advantage may be increased. For example, this may prevent the device from shifting around with respect to the sternum. It may also help provide a consistent, tight fit, which may assist with healing. In some instances, it may be desirable for the underlying tissue to hold onto a body of the sternal device. If a subject's patient can latch onto or grow into or form a fibrous attachment to the central body of the sternal device, the connection will become stronger, and the device may be more difficult to dislodge.

Loose Connections

The sternal device may be designed to fit a body of a subject, rather than making the body conform to the device. For example, a sternal device may fit around a sternum and may conform to the sternum of a subject.

In some embodiments, it may be desirable for there to be loose connections between a central body of a sternal device and the male sutures. These loose connections may be provided where the male suture takes off from the central body and/or where the male suture is received by the central body. Thus, a sternal device on the male and female side may be loose, or may have play to assist with setting the device into position. Once in proper position, the device may be tensioned. As tension increases, movement may decrease.

In some embodiments, a male and/or female base may be connected to a male and/or female stem respectively. At least one of the male or female bases may be configured to enable a male suture to change orientation at the male or female base with respect to the male or female stem to which the male or female base is connected. The male sutures may change orientation at the male or female base within a restricted range. The male or female base may have a low profile with respect to the rest of the central body.

Figure 12:
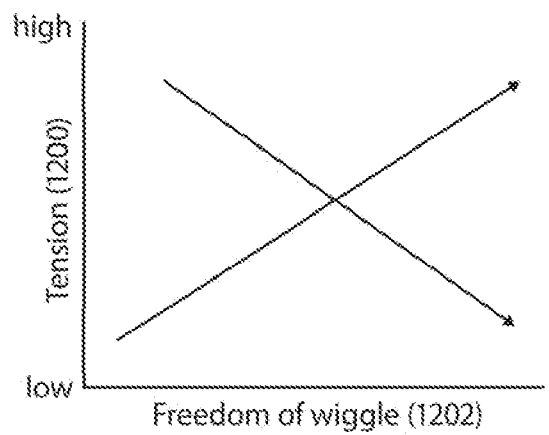
FIG. 12 shows a relationship between tension and freedom of wiggle for a sternal device joint.

FIG. 12 shows a relationship between tension 1200 and freedom of wiggle 1202 generally for a sternal device joint. Typically, an inverse relationship is provided so that when tension is high, there is less freedom of wiggle, and when freedom of wiggle is high, there is less tension.

Thus, when a sternal device is tightened about a sternum, the sternal device may conform to the shape of the sternum and/or other anatomical features without exerting stresses on the body that would be detrimental to the body. As the tension is increased movement of the device may be decreased. Therefore, once the device is tensioned to a desired amount, there may be little system movement that occurs. This may provide an optimal healing environment for bone.

A suture may connect to a main body via a male or female base, or may be directly connected to a male or female stem. Any of these connections may be integral or separable. For example, a suture may be snap fit into a connection, screwed into a connection, crimped into a connection, may be connected with an adhesive, may be clamped within a connection, may be locked into a connection, may be melted into a connection, tied into a connection, impaled into a connection, or connected in any other manner.

Figure 13:
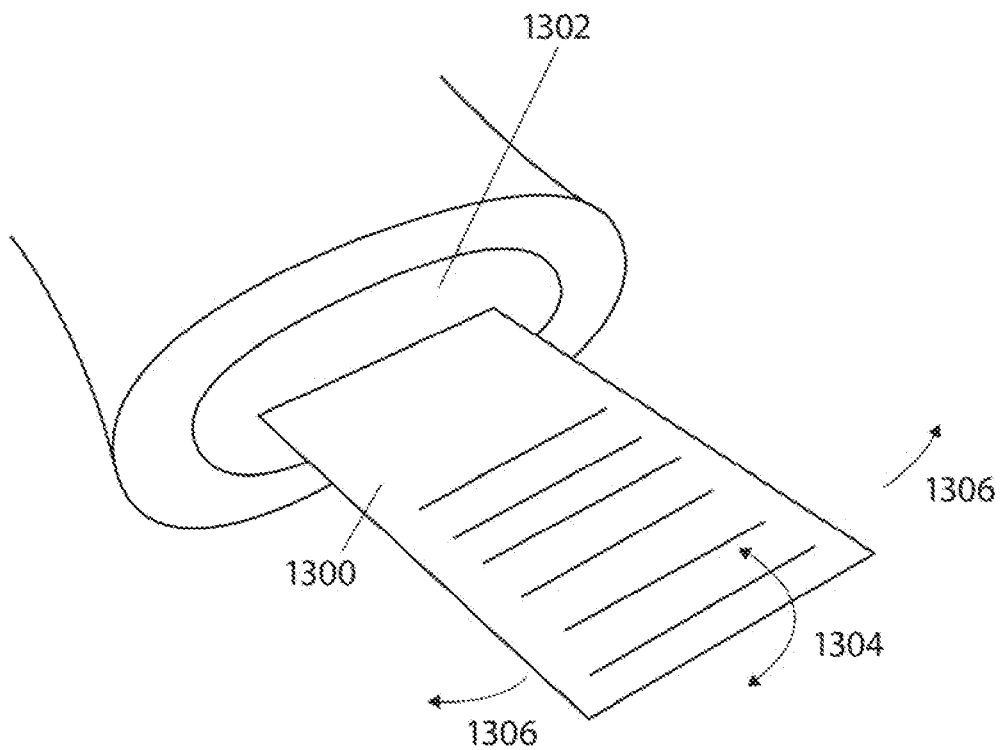
FIG. 13 illustrates a suture connected to a body.

FIG. 13 illustrates a suture 1300 connected to a main body. The suture may be connected so that it may have a loose fit within the socket 1302. The socket may be a male socket and/or a female socket. The suture may be provided within the socket so that when a load is applied to the male and/or female side, the freedom of the system may stop and the suture won't wiggle. This may provide a settled stability within the system.

The suture may have one or more degrees of freedom of wiggle. For example, the suture may be free to move up and down 1304 with respect to the socket. The suture may also be able to move side to side 1306 with respect to the socket. In some alternate embodiments, the suture may also move back and forth with respect to the socket. The loose fit may assist with any of the degrees of freedom. The degrees of freedom may be limited to one, two, or more of the above.

The suture may be connected to the body with the socket so that the sternal device has a low profile. The socket might have a lower profile if it is flat or shaped like a flattened oval. It may or may not have free range of motion like a ball and socket type joint. In some instances, the connection might just have the ability to have a certain range, such as 20 degrees in any direction.

Figure 14:
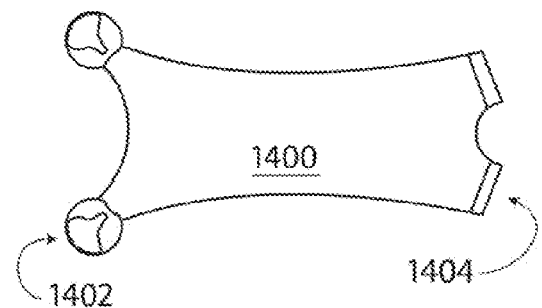
FIG. 14 shows a sternal device body with male and female bases.

FIG. 14 shows a sternal device body 1400 with male 1402 and female bases 1404. The male and female bases may be configured to provide at least one degree of freedom of movement for a suture that may extend from a male base and be received by a female base. A male suture may change orientation at a male or female base within a restricted range. For example, a male suture may rotate side to side within a restricted range. Alternatively, the male suture may angle up and down within a restricted range. In some instances, the male suture may have freedom of motion within two dimensions (side to side and up and down) within a restricted range.

In some instances, a sternal device body may have a male side and a female side. The male side may include male bases, and a female side may include female bases. In some instances, the male side may be on one side of a sternal device body about a vertical axis of the sternal device body and the female side may be on the other side of the vertical axis. Alternatively, the male side may be on one side of a sternal device body about a vertical axis of the sternal device body and the female side may be on the other side of the vertical axis.

Male Connections

A male suture may take off from a male base of a central body of a sternum repair device. The male base and/or male suture may be configured to allow the male suture at least one degree of movement with respect to the male base and/or corresponding male stem.

Figure 15:
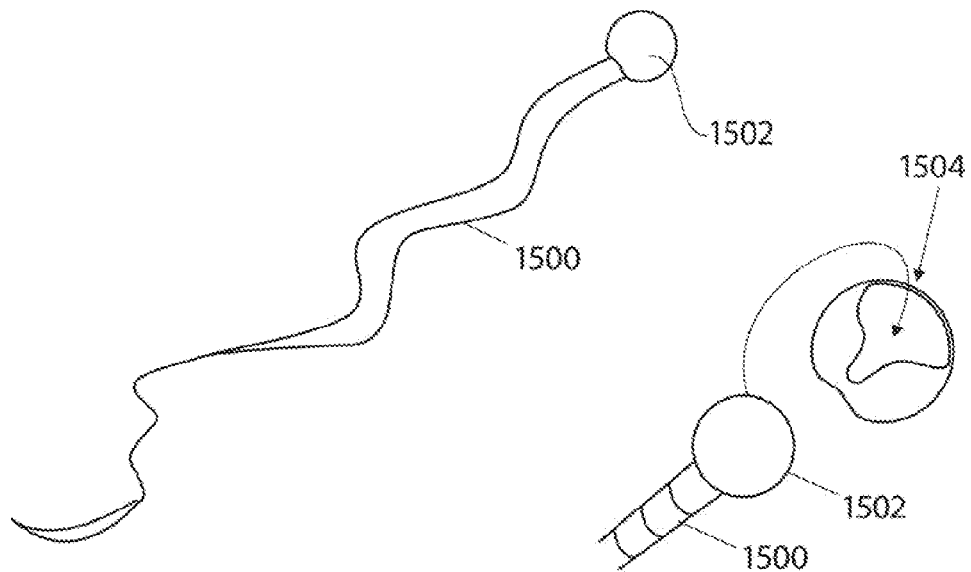
FIG. 15 shows a male suture with a ball and socket joint.

FIG. 15 shows a male suture 1500 with a ball 1502 and socket 1504 joint in accordance with an embodiment of the invention. A male suture and male base may form a ball and socket joint similar to a configuration used for a keychain with balls that may slip into a rounded holder. The male suture may click into the male base and be secured within the male base while having freedom to rotate within a limited range within the ball portion of the base. In some embodiments, when a male suture is clicked in, it can not be backed out. Alternatively, in some instances, it may be backed out in controlled situations.

Figure 16:
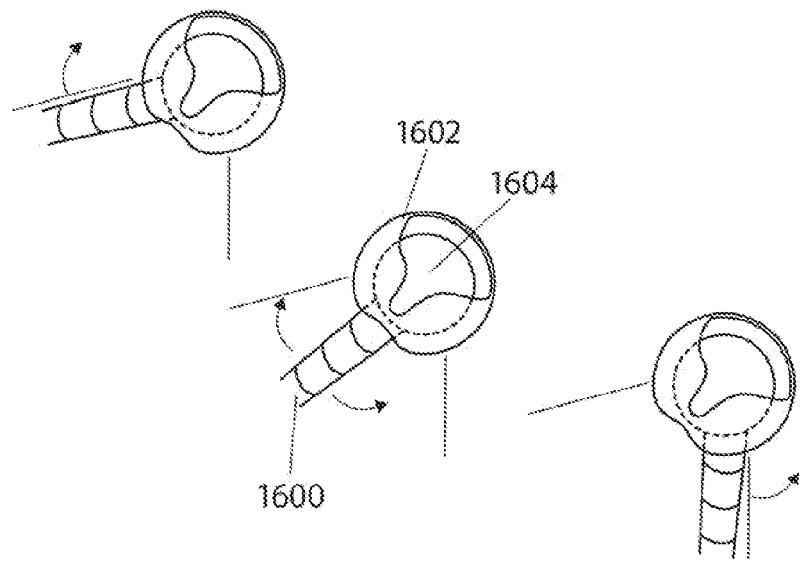
FIG. 16 shows a male suture connected to a male base of a sternal device.

FIG. 16 shows a male suture 1600 connected to a male base 1602 of a sternum repair device. The male suture may rotate within the male base along a limited range of degrees. For example, the male suture may rotate to a left side, then to the middle, and then to the right. Using a ball 1604 and socket time joint may advantageously allow such motion without providing sideways stresses on the device or body. It may allow settling of the device once the device is tightened, so that it does not cause twisting of the central body or binding of the male/female mating.

In some instances, a ball and socket type joint may be round and have a spherical shape. Alternatively, variations may be provided with varying degrees of freedom where different shapes may be utilized, including flat shapes and/or elliptoids. In some instances, the ball and socket joint may have very small dimensions, e.g., such that a maximum dimension may be about 0.3 cm or less, 0.2 cm or less, 0.1 cm or less, 0.07 cm or less, 0.05 cm or less, 0.01 cm or less, 0.005 cm or less, or about 0.001 cm or less. Preferably, the male base and suture may have a low profile with respect to a sternum when used.

The ball and socket joint describe an embodiment where a male suture may click into a male base. Alternatively, the male suture may be integral to the male base.

If the male suture may click into the male base, this may advantageously allow customizable lengths of male suture to be placed. For example, in some instances, a user may need 18 inches vs. 12 inches of suture. Another advantage may be that the suture may be placed around the sternum and then clicked into the device. This may keep the body and other suture from flipping around while a user is operating. A separable male suture may also provide increased potential for modular components like different body shapes with different suture lengths. In some instances, this may also allow for easier packaging. Furthermore, it may simplify production, e.g., if the body and male suture are molded separately. They may be joined at the factory, or may be shipped separately.

If the male suture is integral to the male base, this may advantageously provide a simplicity of design. This may also reduce the number of steps associated with assembly and installation into the body. Having a male suture integral to a male base may also remove another possible point of failure or diminished performance, and may be cheaper to produce.

Although such a configuration may preferably be used for a male base and/or connection, it or various of it may be applied to a female base and/or connection as well. Similarly, any of the female connections described or variations thereof may also be applied to male bases.

Female Connections

A male suture may be received by a female base of a central body of a sternum repair device. The male base and/or male suture may be configured to allow the male suture at least one degree of movement with respect to the male base and/or corresponding male stem.

Figure 17:
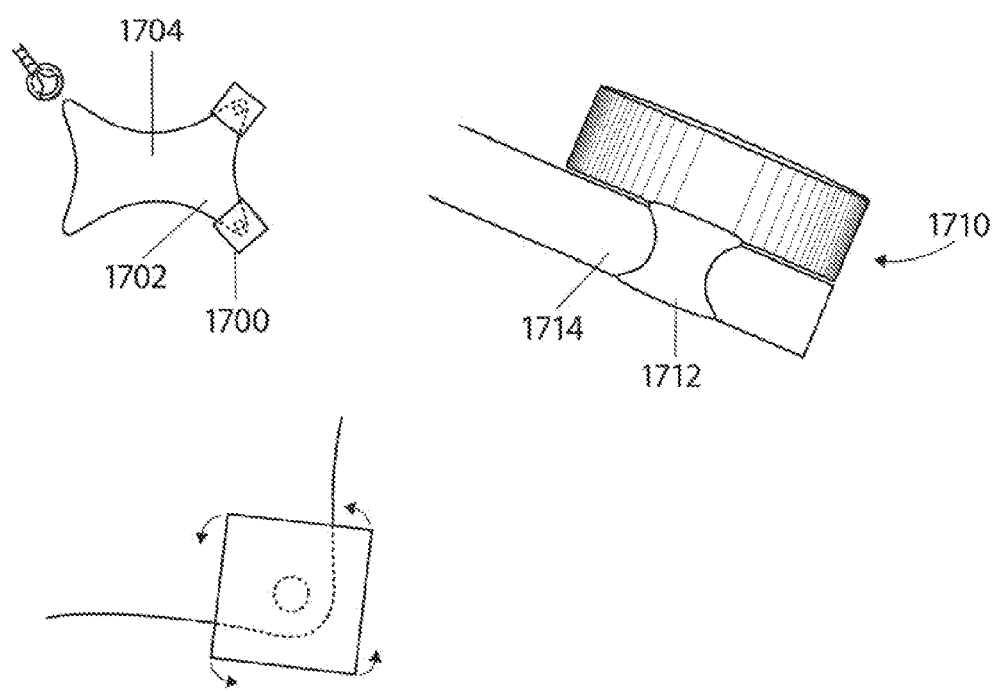
FIG. 17 shows a female base of a sternal device in accordance with an embodiment of the invention.

FIG. 17 shows a female base 1700 of a sternal device in accordance with an embodiment of the invention. The female base may be on a female stem 1702 of a central body 1704 of the sternal device. The female base may swivel on the female stem. In some instances, the female base may have the freedom to swivel completely around the female stem. In other embodiments, the female base may only be configured to swivel within a restricted range. For instance, protrusions, or other stopping mechanisms may be provided that may prevent the female base from swiveling entirely.

The female base may have any shape that may accept the male suture. Although a rectangular or square shaped female base may be displayed, the female base may alternatively be shaped as a triangle, circle, ellipse, pentagon, hexagon, octagon, or any other regular or irregular shape. The female base may have rounded edges. In some instances, the female base may be contoured to not get caught on anything and allow a smooth turn.

FIG. 17 also shows a side view of the female base 1710. The female base may be held in place by a pin or axis 1712 that may attach the female base to the female stem 1714. The pin may allow the female base to swivel around with respect to the stem. The pin may be fixedly attached to the female base and may rotate with respect to the stem; the pin may be fixedly attached to the stem and the female base may rotate with respect to the pin; or the stem, pin, and female base may all rotate with respect to one another. In some instances, the pin and the female base may be formed of one piece.

Preferably, the female base may have a low profile. In some instances, the female base may be disposed over the female stem. It may or may not overhang part of the female stem. Alternatively, the female base may be provided below the female stem, or may be within the female stem or adjacent to the female stem so that it does not protrude over or below the stem.

Figure 18:
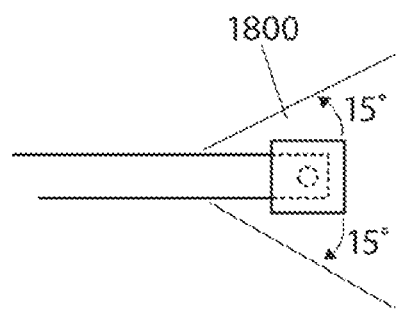
FIG. 18 shows a range of rotation for a female base.

FIG. 18 shows a range of rotation for a female base 1800. For example, in some embodiments, the female base may rotate about 15 degrees to meet up with the male suture effectively. In other embodiments, any degree of rotation may be permissible, which may include about 5 degrees, 10 degrees, 20 degrees, 30 degrees, 45 degrees, 60 degrees, 90 degrees, 120 degrees, 150 degrees, 180 degrees, 270 degrees, or 360 degrees of rotation. In some instances, the rotation may only be provided on one side, while in other embodiments, it may be provided on both sides.

Figure 19A:
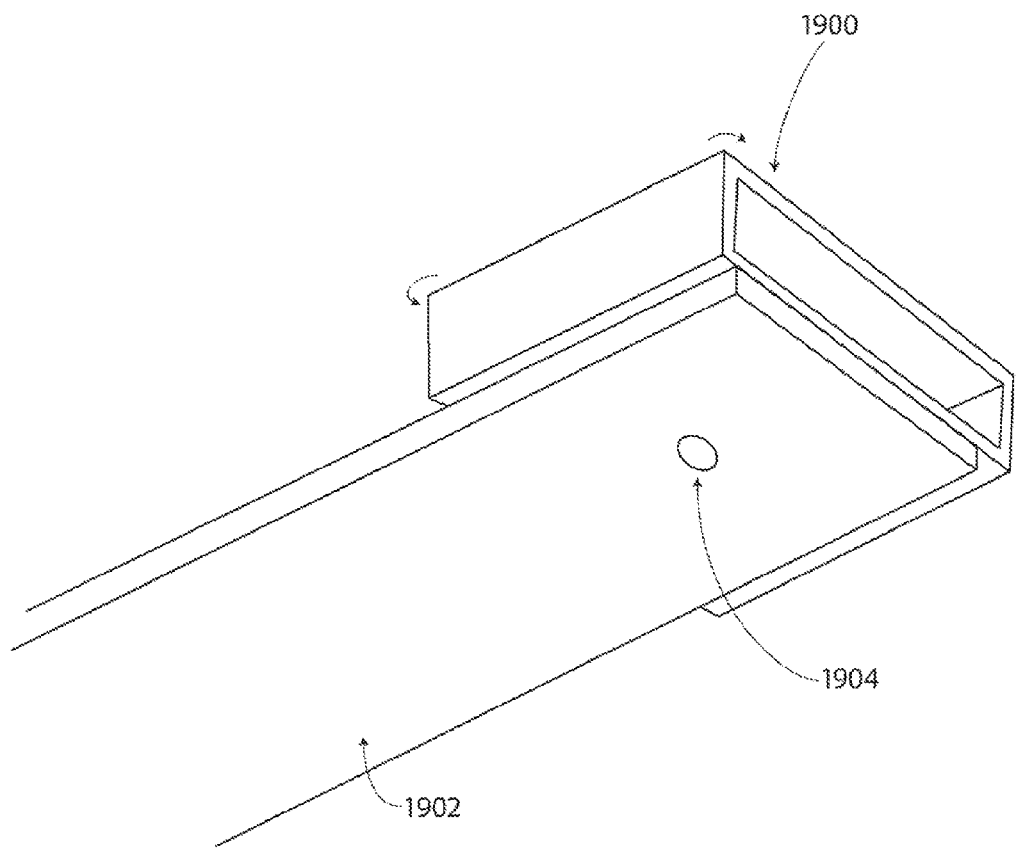
FIG. 19A shows a female base on a female stem, which may move along a restrictive path relative to the stem.

FIG. 19A shows a female base 1900 on a female stem 1902, which may move along a restrictive path relative to the stem. In some instances, the female stem may be elongated. The female stem may be flexible and thin.

A female base pivot 1904 may be provided which may allow some small adjustments on the female side. The female base may be shaped to depend on the shape of the male suture. For example, if a flat male suture is provided, the female base may have a flat shape. Alternatively, if a round male suture is provided, the female base may have a round shape. The female base may be any shape that may receive the male suture. In some instances, the female base may have an outer surface and an inner surface. In some instances, the shape of the outer surface and inner surface may match (e.g., both may be round, or both may be flat). Alternatively, the shape of the outer and inner surfaces may be different (e.g., the inner surface may be rounded, while the other surface may be provided a more flat, contoured shape). The inner surface of the female base may match the shape of a male suture.

Figure 19B:
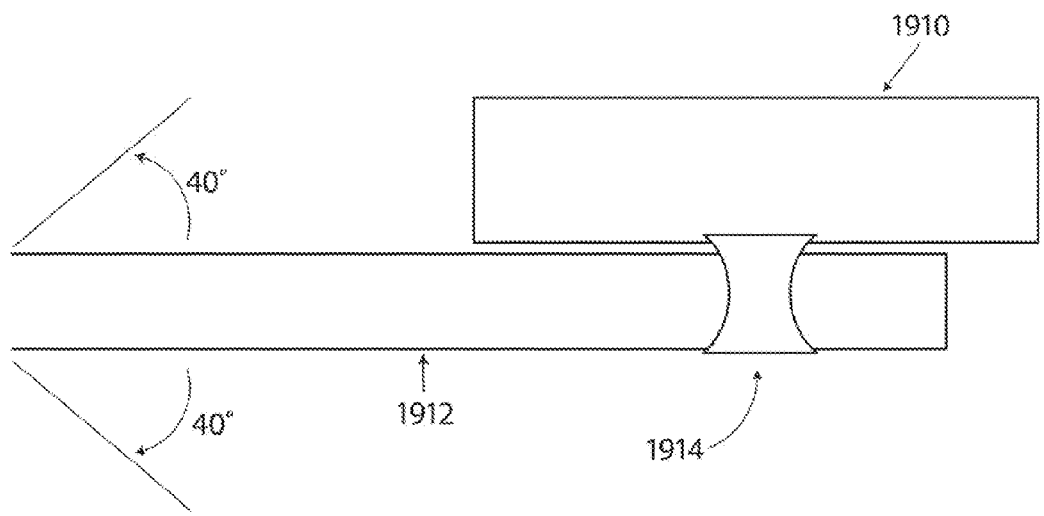
FIG. 19B shows a side view of a female base on a female stem.

FIG. 19B shows a side view of a female base 1910 on a female stem 1912. The female stem may be thin and/or flexible. In some instances, the female stem may bend or flex upwards and/or downwards. In some embodiments, the female stem may flex about 40 degrees upwards, and/or downwards. In other embodiments, the female stem may flex about 5 degrees, 10 degrees, 15 degrees, 20 degrees, 30 degrees, 35 degrees, 45 degrees, 50 degrees, 60 degrees, or about 90 degrees upwards and/or downwards. The stem may flex to fit the contour of a sternum and/or any other anatomical feature.

In some instances, the stem may be constructed of a material that may bend, and then retain its shape after being bent. In such embodiments, the stem may be wrapped around to fit the contour of a sternum and then may retain that shape in the absence of outside force.

In some instances, a female base may only swivel from side to side. In some instances, the female base may swivel about a pin 1914. In other embodiments, the female base may also angle upwards or downwards with respect to the female stem within a limited range.

Figure 20:
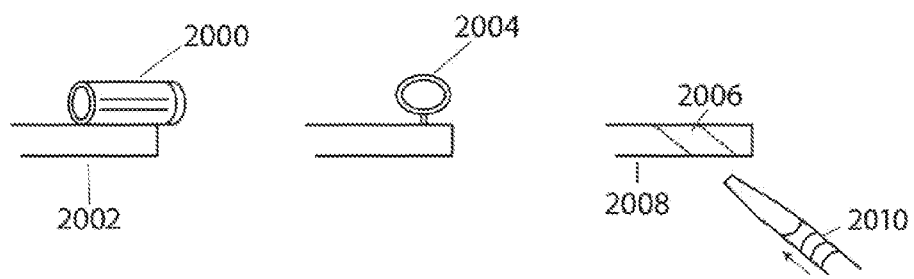
FIG. 20 provides views of additional examples of female bases and stems.

FIG. 20 provides views of additional examples of female bases and stems. In one embodiment, a round female base may 2000 be provided on a female stem 2002. This may be advantageous when a round male suture is used. The round female base may form a tube or cylinder. In other embodiments, the round female base may have a conical shape. Alternatively, the round female base may form a loop or ring 2004.

In other embodiments, the female base 2006 may be integrated into a stem 2008. In one example, the female base may be provided at an angle within the stem so that the male suture 2010 may pass through the stem. Any angle may be provide, e.g. 5 degrees, 10 degrees, 15 degrees, 30 degrees, 45 degrees, 60 degrees, 80 degrees, or 90 degrees.

For any of the embodiments described, a male suture may include male locking features. A female base may have corresponding female locking features which may engage with the male locking features and restrict the motion of the male suture in at least one direction. For example, the female base may be configured to accept the male suture so that the male suture can only pass through in one direction.

In other embodiments, the male suture need not include male locking features. The female base may include female locking features or any sort of retaining mechanism that may engage with the male suture and restrict the motion of the male suture in at least one direction. In some instances, the female retaining mechanism may prevent the male suture from moving in either direction. For example, the female retaining mechanism may include some sort of clamp, teeth, crimp, pin or hook that may catch onto the male suture and hold it in place when so directed by a user. Possible suture configurations are discussed in greater detail below.

Figure 21:
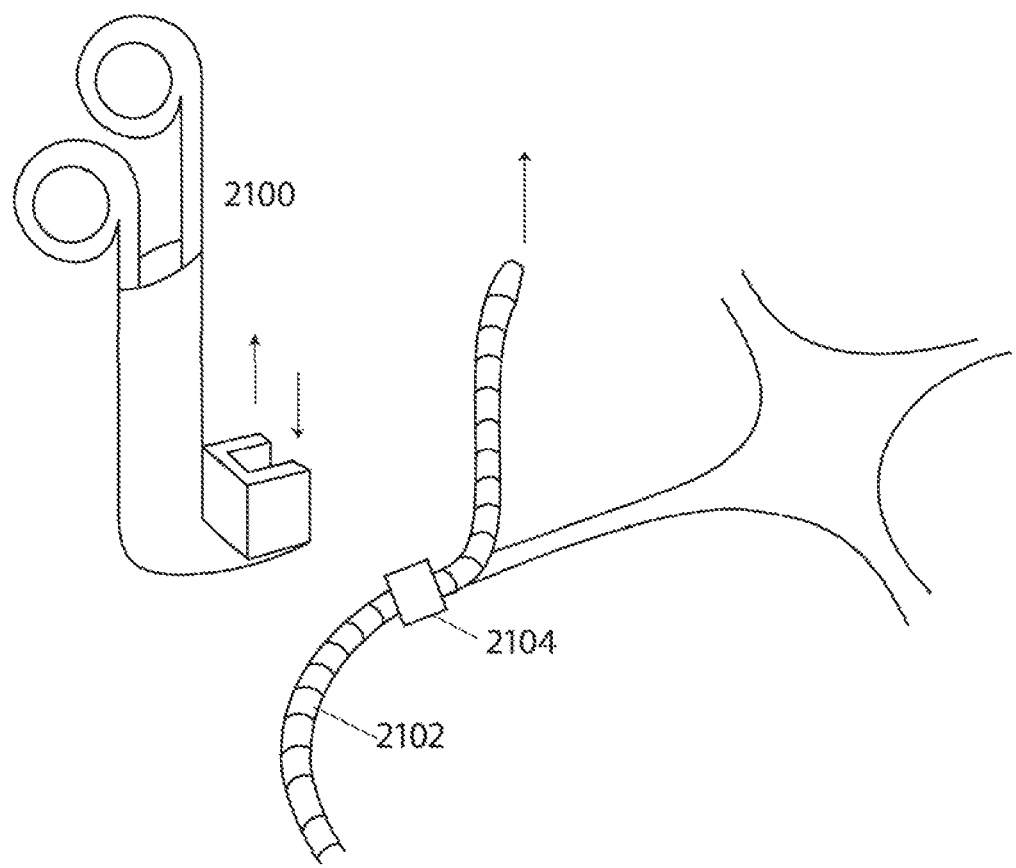
FIG. 21 shows an example of a tool that may be used to tighten a male suture along a female base.

FIG. 21 shows an example of a tool 2100 that may be used to tighten a male suture 2102 along a female base 2104. The tool may be configured to both tighten the male suture and to cut off excess suture so that it is flush with the female base. The tool may have a tightening mechanism which may draw the male suture through the female base a predetermined amount and/or retain the male suture at its present position. Thus, it may incrementally tighten the male suture. Alternatively, it may have a mechanism that may allow it to continuously tighten the male suture. The tool may also have a cutting mechanism which may cut through the male suture. The cutting mechanism may be positioned on the tool to cut the male suture flush with the female base.

The tool may include a tension dial to dial in whatever tension is required. Alternatively, it could be inherent to the device.

When the male suture is tightened against the female base, the sternal device with flexible male and/or female bases may be configured to allow the device to settle around a sternum (or other anatomical feature) without putting too much stress on the device or the surrounding body.

Although such a configuration may preferably be used for a female base and/or connection, it or various of it may be applied to a male base and/or connection as well. Similarly, any of the male connections described or variations thereof may also be applied to female bases.

Suture

A suture of a sternal device may have any configuration. Preferably, the suture may be formed of a flexible material. Alternatively, the suture may include rigid and/or semi-rigid components. The suture may be configured to bend sufficiently to wrap around a sternum or part of a sternum.

The suture may preferably be formed of a material with sufficient tensile strength to hold together a split sternum and/or other anatomical features. The suture may or may not be configured to stretch when tightened.

The suture may have any major diameter size that may allow it to wrap around the sternum. For example, a diameter of the suture may be about 0.7 cm or less, 0.5 cm or less, 0.3 cm or less, 0.2 cm or less 0.1 cm or less, 0.07 cm or less, 0.05 cm or less, 0.03 cm or less, 0.01 cm or less, 0.005 cm or less, or about 0.001 cm or less.

The suture may have any cross-sectional shape. For example, the suture may have a substantially circular cross sectional shape. Alternatively, it may have an elliptical cross sectional shape, rectangular cross sectional shape, square cross sectional shape, or by substantially flat, like a tape.

In some embodiments, a suture may have any lengths. In some instances, all of the sutures for a sternal device may have the same length, while in other instances, the length at least one suture may vary. In some instances, suture may be selected at a desired length and then connected with a male stem or base to customize the device to the subject. Some examples of suture lengths may include sutures that are about 100 cm long, 80 cm long, 70 cm long, 60 cm long, 50 cm long, 40 cm long, 35 cm long, 30 cm long, 25 cm long, 20 cm long, 15 cm long, 12 cm long, 10 cm long, 8 cm long, or 5 cm long.

Suture materials may have any desired material property, which may include a desired strength, stiffness, flexibility, or elasticity of the suture. For example, the suture may be elastic like a bungee cord type material. Otherwise, it may stretch less, like a thread or string-like material. In some instances, the suture may be formed of a wired or braided structure, which may include wires or fiber.

In some embodiments, the suture may have a substantially smooth surface. Alternatively, the suture may have a texture surface and/or locking features. The textured surface and/or locking features may run along the entire length of the suture, or only along one or more selected portions of the suture. In some instances, the selected portions may be toward a first end of the suture or a second end of the suture.

Figure 22:
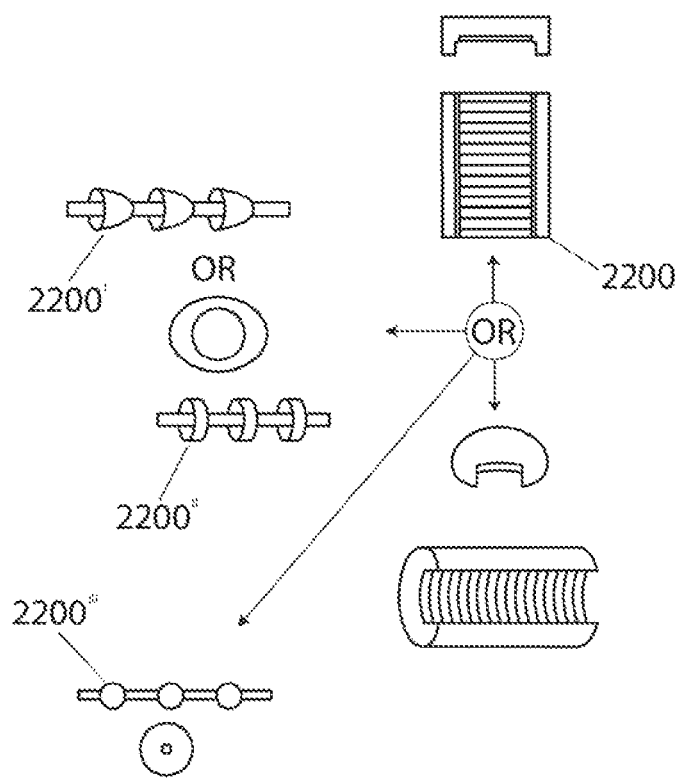
FIG. 22 shows examples of various possible suture configurations.

FIG. 22 shows examples of various possible suture configurations. In some examples the suture may have locking features 2200 such as ball shapes, cylindrical or circular shapes, pointed conical shapes, barbs, roughening, knurling, protrusions, indentations, grooves, ridges, teeth, or any other shape. In some instances, some of locking features (e.g., bumps, teeth or ridges) may be buried so that they do not protrude from the suture. The suture itself may be round or elliptical with hidden locking features which may prevent them from catching on tissue. For example, the suture may include one or more large channel or indentation, in which locking features may be provided. In some instances, the suture may include one or more linkages, like a chain.

Figure 23:
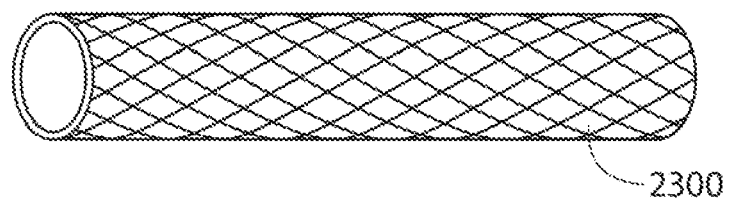
FIG. 23 provides an additional example of a suture configuration.

FIG. 23 provides an additional example of a suture configuration 2300. In some embodiments, a suture may be inlayed with fibers, fine wire, mesh, or other additives which may increase the strength of the suture, and thereby the sternal device. Additives may make the suture stiffer to longitudinal forces and/or provide any other desired material properties, such as stiffness, flexibility, strength, or elasticity to the suture. In some instances, the fibers or other additives may be like mesh used in other applications. It may allow strength without limiting or minimally impacting flexibility.

Such additives may run within the substance of the suture or maybe provided along the surface of the suture.

A suture may be connected to another suture or to a base by various techniques. For example, a suture may be connected to another suture or other component via crimping, soldering, gluing, wedges, locking features, via a sleeve, a shim, an adhered portion, a heat deformed portion, or a melted portion.

Device on Sternum

In accordance with an aspect of the invention, a sternum repair device may be applied on a sternum of a subject. A subject may be human or animal, and may be a patient, or may be involved in testing or research. The sternum repair device may be provided after a sternotomy, when a split sternum has been provided. The sternal device may wrap around the split sternum, to allow the sternum to heal and grow back together.

In alternate embodiments, the sternum repair device or variation thereof may be applied to other similar anatomical features of a subject. Such anatomical features may include a split bone. The sternum repair device may wrap around any tissue (bone tissue or soft tissue) which may require a device to wrap around it to hold it together and/or allow it to heal together.

Figure 24:
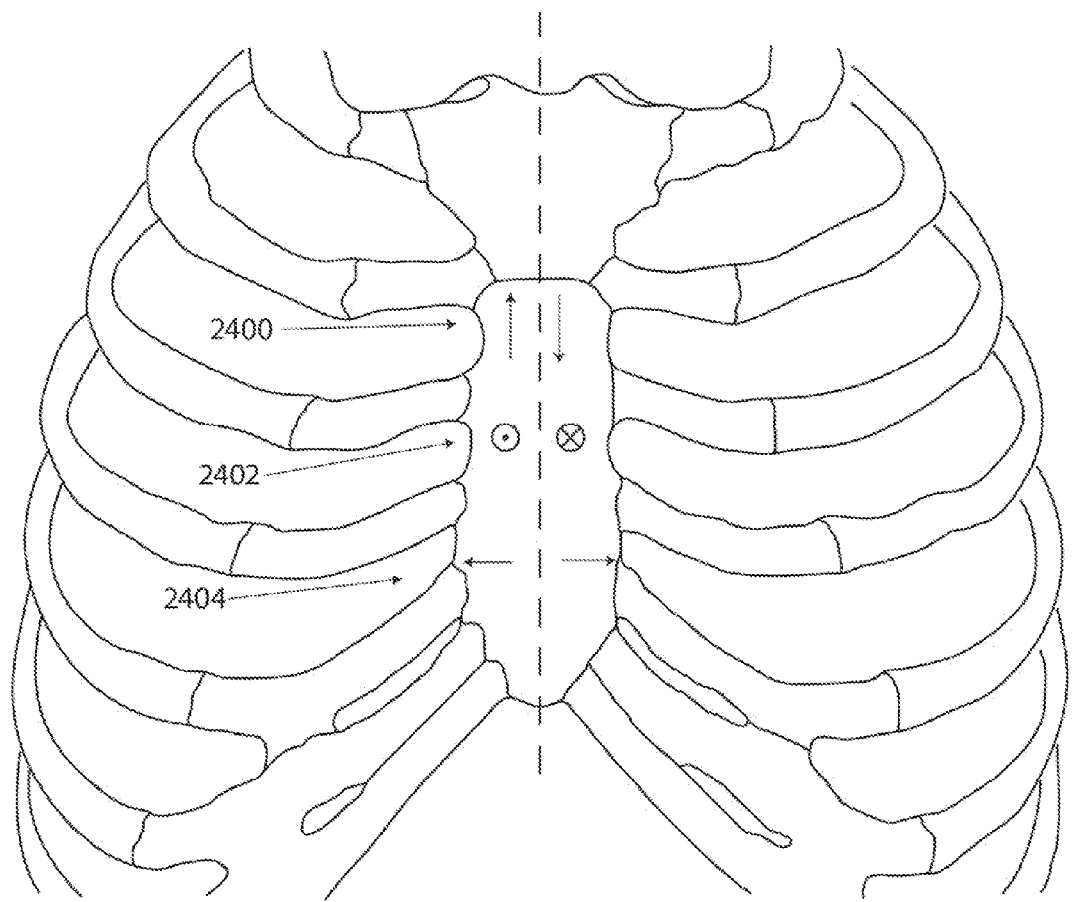
FIG. 24 shows an example of forces at play on a split sternum.

FIG. 24 shows an example of forces at play on separate pieces of a sternum after a sternotomy. Some examples of such forces are cephalad/caudal 2400, anterior/posterior 2402, or lateral 2404 forces.

Preferably, one or more of these forces may be neutralized or reduced using a sternum repair device, to encourage the bone to heal together. Preferably, the sternum repair device will substantially immobilize the separate sternum pieces together.

Figure 25:
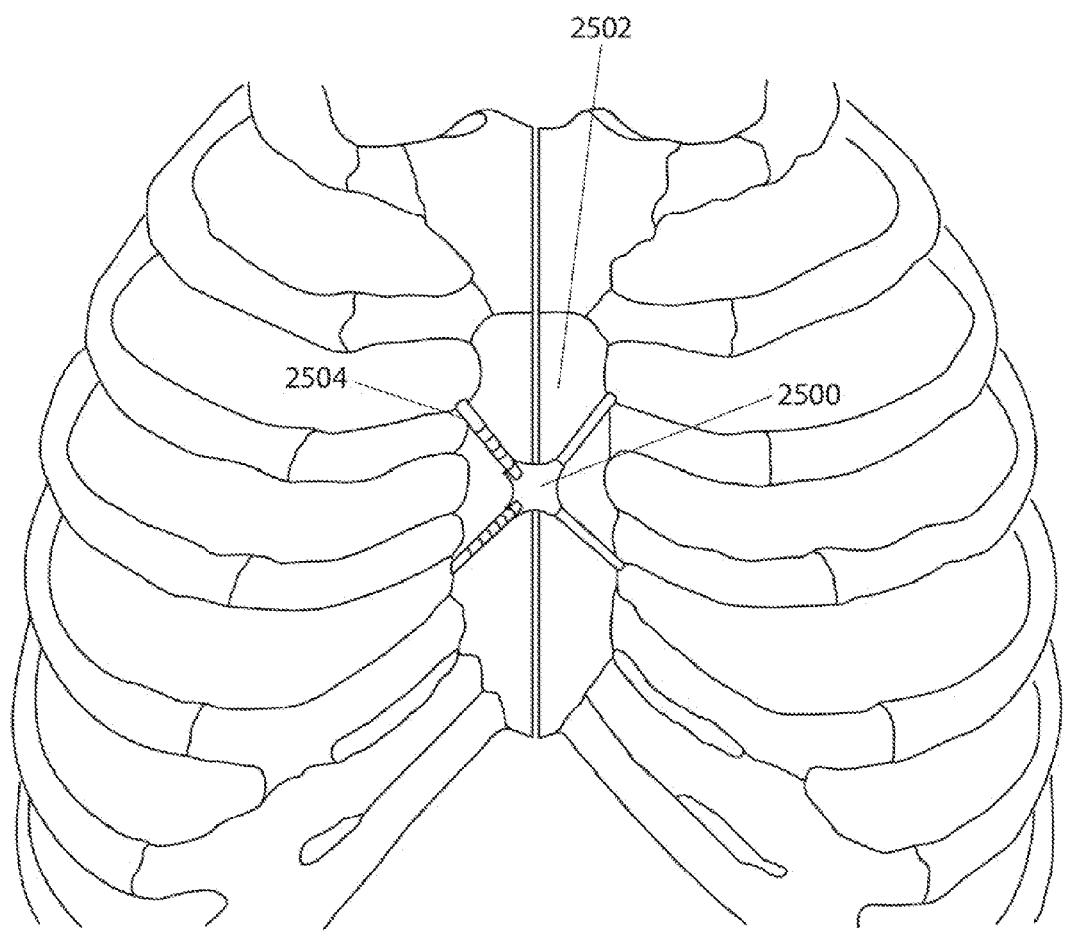
FIG. 25 provides an example of a sternum connecting device disposed on a split sternum.

FIG. 25 provides an example of a sternum connecting device disposed on a split sternum 2502. A median sternotomy may have occurred, where the sternum may be split along the middle of the sternum. A central body 2500 of the sternum connecting device may be placed on an anterior side of a sternum. One, two, or more male elongate members 2504 may extend from the central body, wrap around the posterior side of the sternum and connect to the central body on the anterior side of the sternum. The elongate members may be tightened to hold the separate pieces of the sternum together.

In some embodiments the sternum connecting device may span one, two, or more sets of ribs. In FIG. 25, the sternum connecting device spans two sets of ribs.

Figure 26:
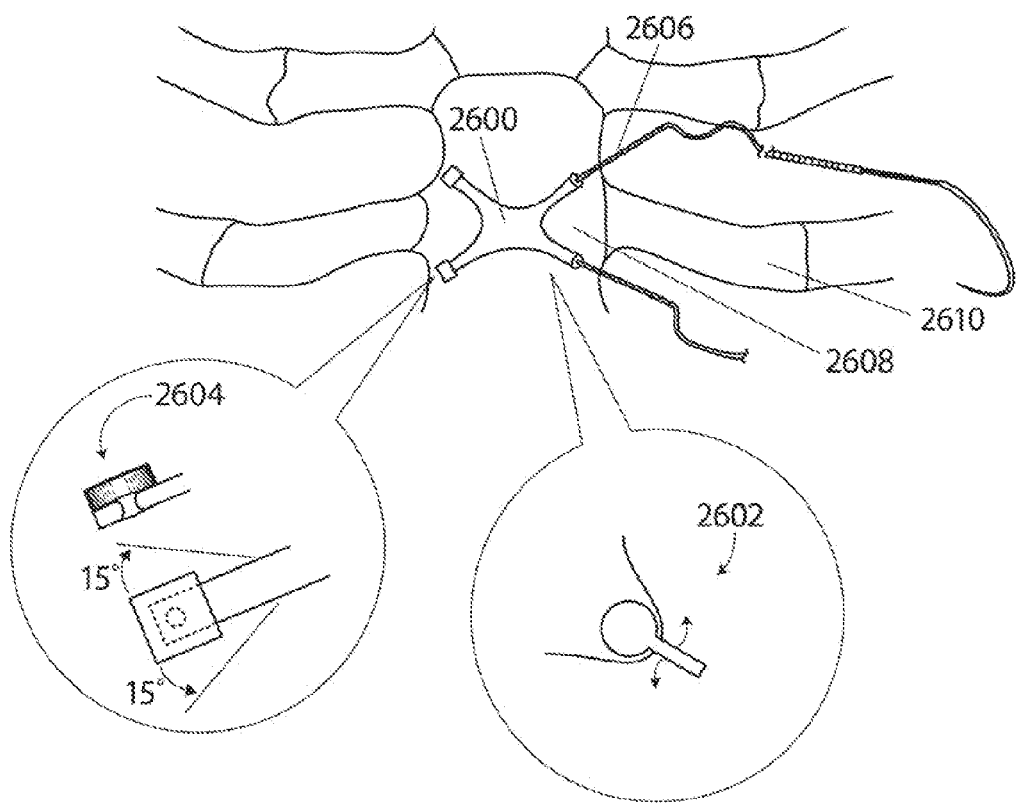
FIG. 26 shows an example of a sternal device with flexible components that can be disposed in a body.

FIG. 26 shows an example of a sternal device with flexible components that can be disposed in a body. The sternal device may have a central piece 2600 with one or more male bases 2602 and one or more female bases 2604. A male suture 2606 may extend from a male base and be received by a female base. The male suture may wrap around the sternum 2608. In some instances, the male suture may be positioned to wrap around the suture so that it passes over a rib or under a rib 2610.

The male and/or female bases may be configured to allow the male suture to change orientation at the male or female base with respect to the central body to which the male or female base is connected. In one example, two male bases may be provided and two female bases may be provided. The male bases may utilize a ball and socket type connection. The female bases may utilize a swivel type connection. Alternate loose-fitting or movable connections may be utilized.

The male suture may be flexible. In some instances, it may be about 2-3 mm in diameter. The male suture may include locking features, such as teeth, which may engage with the female base. The male suture may also include an engagement zone, which may narrow the male suture. The engagement zone may or may not include locking features. In some instances, the engagement zone does not have teeth so that it rights itself into the female base.

Optionally, a needle may also be provided. The needle may be connected to the engagement zone or the male suture.

Figure 27:
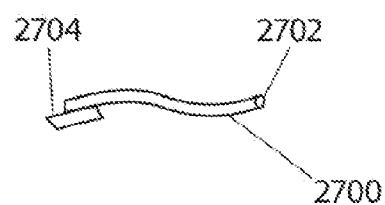
FIG. 27 provides a view from a bottom of a body to view a profile of a sternal device.

FIG. 27 provides a view from a bottom of a subject's body to view a profile of a sternal device 2700. The view may be provided when looking at a patient from a foot of a bed, when the patient is lying on his back. The device may preferably have a shape that may mirror the contour of the sternum. This may be contrasted with an alternate embodiment that may utilize a flat piece.

Preferably, the contoured device may have a low profile with respect to the sternum. Any male and/or female parts may also be configured not to protrude from the device by a large amount and/or may be contoured to minimize or reduce internal irritation. In some instances, the male 2702 and/or female 2704 base may be positioned over the side of the sternum. In such situations, the male suture may interact with the central body on the sides so that they are not on the anterior or posterior side of the sternum. Alternatively, they may be along an anterior surface or a posterior surface of the sternum. Thus, male and/or female stems may or may not go over the edge of a sternum to hide, so that the subject need not feel the device on the male or female side. When the male and/or female engagement mechanisms are out over the edge of the sternum, they may be hidden from palpation. The male and/or female base may be configured so that they are under a central body portion of the sternum, so that they may at least lie partially between the sternum and an exterior portion of the central body.

Figure 28:
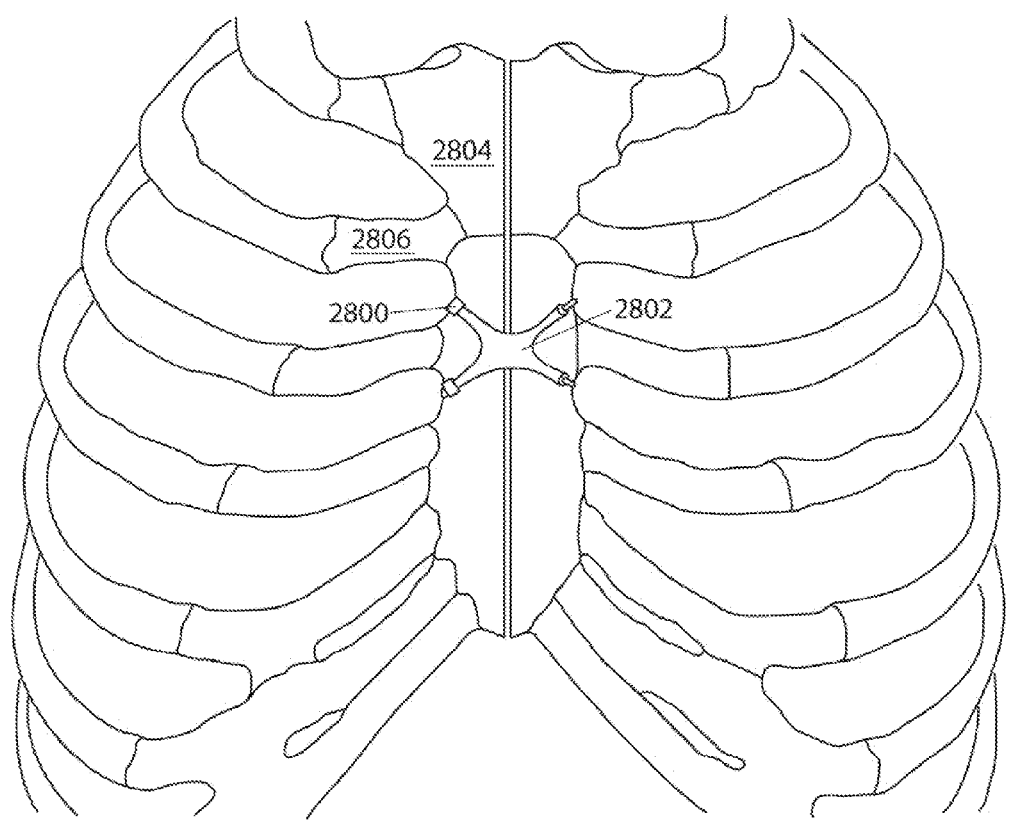
FIG. 28 shows a sternal device on a sternum in accordance with another embodiment of the invention.

FIG. 28 shows a sternal tissue connecting device on a sternum in accordance with another embodiment of the invention. The tissue connecting device may be positioned to connect separate pieces of the sternum. In some instances, elongate members 2800 may extend from a central body 2802 and wrap around the sternum 2804. The angle created by the elongate members as they extend from the central body may be variable. This may depend on the number and/or size of ribs 2806 that the device spans. The angle may be variable within human anatomy. This may allow a built-in customization of the sternal tissue connecting device.

Some examples of the angle that may be created by the sutures may include 5 degrees, 10 degrees, 15 degrees, 30 degrees, 45 degrees, 60 degrees, or 75 degrees. If a greater number of ribs are spanned or the central body is smaller, the angle may be increased.

Sternal Device Variations

Figure 29A:
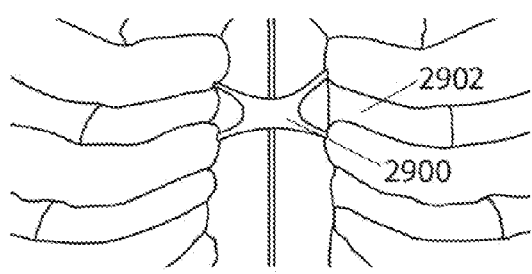
FIG. 29A shows an example of a sternal device spanning one set of ribs.

FIG. 29A shows an example of a sternal device 2900 spanning one set of ribs 2902. A system for connecting tissue may be provided. In some embodiments, the central body of a sternal device may be fitted to span one set of ribs. The stems may be at a length, where the sutures may be used to span one set of ribs.

Figure 29B:
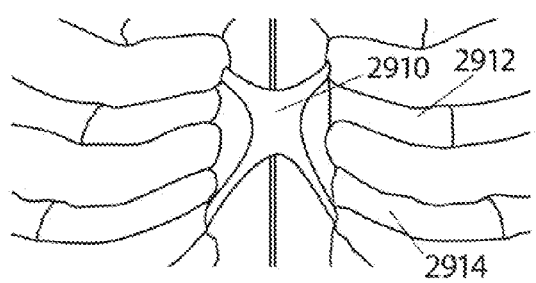
FIG. 29B shows an example of a sternal device spanning two sets of ribs.

FIG. 29B shows an example of a sternal device 2910 spanning two sets of ribs 2912, 2914. In some embodiments, the central body of the sternal device may be fitted to span two sets of ribs. For instance, the stems provided on the central body may be longer when used to span two set of ribs, than for a central body used to span one set of ribs.

In some embodiments, the stems may be integral to the central body. The central body may be selected to fit a particular sternum. For example, larger central bodies may be selected to fit a larger sternum. Alternatively, the stems may be separable from a central region of the central body, or from one another. In such situations, different sizes or shapes of stems may be swapped out to accommodate sternum sizes and/or arrangements. In some instances, the length of a stem itself may be adjustable to fit the desired sternum. For example, the stem may have a sliding and locking feature, or some sort of telescoping feature that may enable it to change lengths.

In other embodiments, the angles of the stems with respect to one another may be adjustable. For example, the stems may be attached to one another or to a central region such that their angles or positions can be adjusted. In some instances, angles or positions may be adjusted within a limited range.

The separable pieces may be lock-fitted together, or may snap together, screw together, or come together in any other mechanical manner. In some instances, a stem may be selected to match the sizes of the other stems, while in other embodiments, a stem may be selected to match an anatomical feature, which may or may not result in it matching the other stems.

Stems may also be selected of the same or varying materials. In some instances, it may be more desirable to have a more flexible stem while in other embodiments it may be more desirable to have a more rigid stem.

In other embodiments, the same central body may be utilized for various sternum sizes and/or rib spanning or other application techniques. The suture size and/or arrangement may vary to accommodate different sizes or ranges. This may provide restricted freedom, which may allow a user to space different rib widths, which allows use on various patient body types, and allows insertion to be easier.

Figure 30:
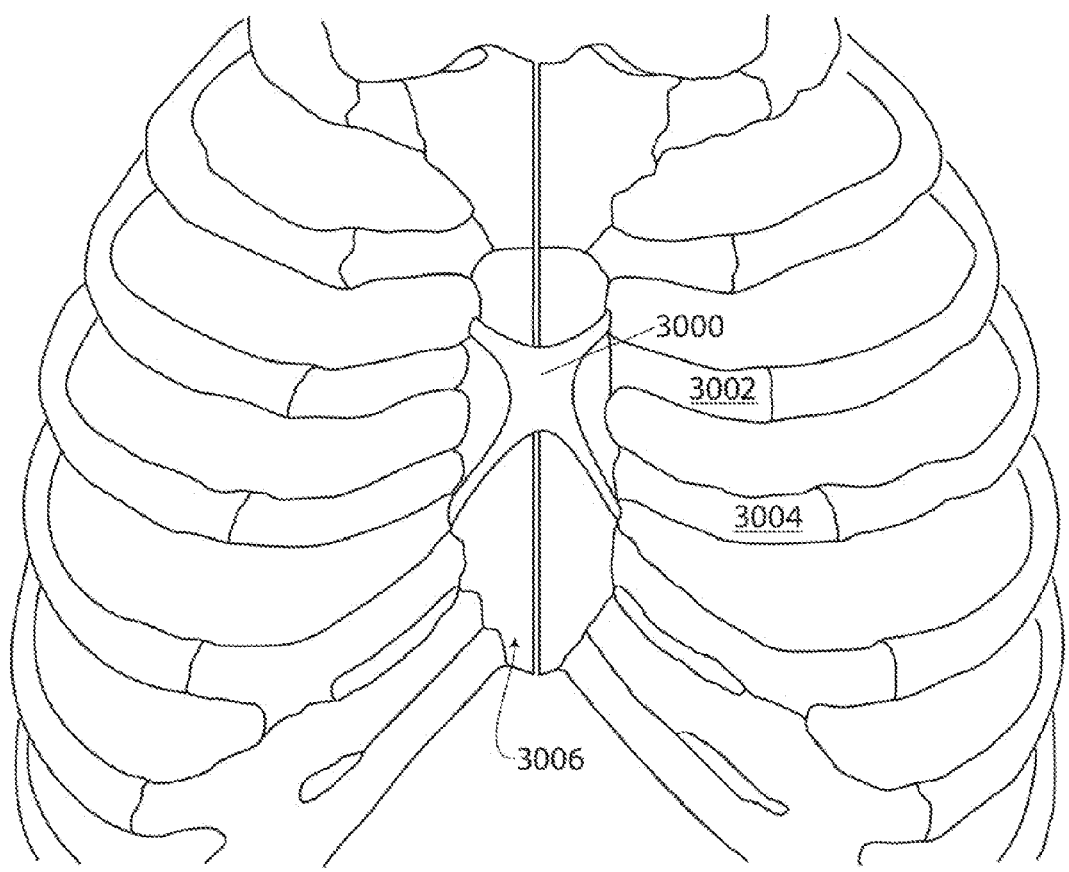
FIG. 30 shows an example of a sternal device spanning two ribs on a sternum.

FIG. 30 shows an example of a sternal device 3000 spanning two ribs 3002, 3004 on a sternum 3006. A sternal device may be placed to span any number of ribs or any placement of ribs. In some instances, one, two, or more sternal devices may be utilized following a sternotomy.

A system for connecting two tissues, such as two bone tissues of a split sternum may include a central body which may have a plurality of male stems and a plurality of female stems. Optionally, the central body may include a plurality of male bases connected to the male stems and a plurality of female bases connected to the female stems. The system may also include a plurality of male sutures, wherein the male sutures may take off from a male base of the central body, wrap around two tissues (such as separate pieces of a sternum) and is accepted by a female base of the central body.

In some embodiments, at least one of the male stems, male bases, female stems, or female bases may be separable from the central body. In some embodiments, at least one of the male stems, male bases, female stems, or female bases may be replaceable with corresponding components of different size. For embodiments with longer stems, the stems may be "clip on" or "snap on" to facilitate placement. Alternatively, the male and female stems may be integral to the central body.

Figure 35:
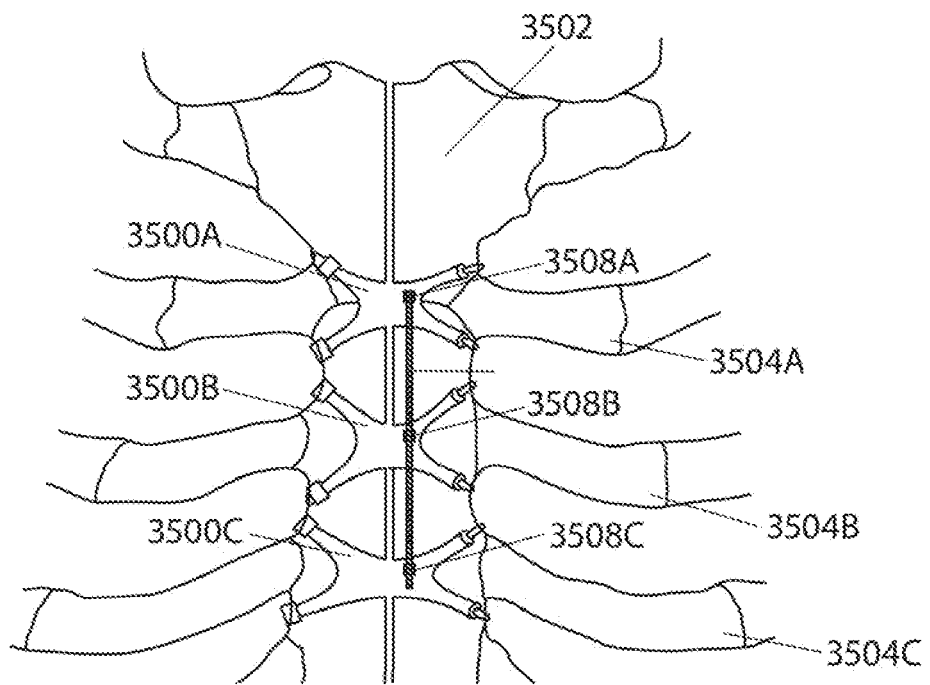
FIG. 35 shows a linking bar provided in accordance with an embodiment of the invention.

FIG. 35 shows an example of a linking bar system in accordance with an embodiment of the invention. A linking bar may simulate an external fixator on the sternum.

In some embodiments, a plurality of sternal devices 3500a, 3500b, 3500c may be provided. The sternal devices may connect pieces of a sternum 3502 and span different sets of ribs 3504a, 3504b, 3504c. A linking bar 3506 may connect the plurality of sternal devices. In some embodiments, the linking bar may be connected to the central body of a sternal device via a locking mechanism 3508a, 3508b, 3508c.

In some embodiments, a single linking bar may be used to connect all of the sternal devices in a subject. In another embodiment, multiple linking bars may be used to connect multiple sternal devices. In some embodiments, one, two, or more linking bars may be provided between sternal devices. Correspondingly, one, two or more linking bar locking mechanisms may be provided on a sternal device. In some embodiments, the linking bar may be made from a soft or hard material, and may serve to link the two central bodies together. In some embodiments, the linking bars may be formed of or incorporate other materials described elsewhere herein. The linking bar may have an elongated shape. In some embodiments, the linking bar may include teeth, bumps, grooves, ratchets, holes, protrusions, or any other surface feature that may assist with interfacing the linking bar with the locking mechanism. The locking mechanism may include corresponding features that may allow the linking bar to be retained. In some embodiments, tension may or may not be exerted on the linking bar.

In some embodiments, the linking bar may be applied so that it runs parallel or substantially parallel to the sternum. Alternatively, it may be applied so that it is at an angle to the sternum. If a plurality of linking bars are applied, they may be parallel to one another. Alternatively, they may be at an angle to one another or may cross over one another. In some instances, a linking bar may be parallel or substantially parallel to a split in the sternum.

A linking bar system may simulate a complex weave closure to provide additional stability to the sternum and distribute forces across the construct. It may have a flat geometry. In some embodiments, it may be held together with a similar mechanism as the closure. It may be applied after all of the sternal devices are in place. Alternatively, it may be applied as sternal devices are being applied, or pre-applied before the sternal device is applied to the sternum.

Materials for Device

The various components of the sternal device may be manufactured from any material with desired material properties. For examples, any of the central body, the male stems, the female stems, the male bases, the female bases, the male sutures, the male engagement zones, or delivery needle may include components formed from metal (e.g., steel, iron, aluminum, copper, silver, gold, titanium, etc. or combinations or alloys thereof), plastic, rubber, thread, or so forth.

In some embodiments, different degrees of stiffness, flexibility, or other material qualities may be desired for different components. For example, for a central body, it may be desired for the shape to be firm, stiff, or molded. Alternatively, it may be desired to be flexible. In some instances, it may be desirable for stems of the central body to be more flexible than the central region of the central body. In some instances, it may be desirable for male sutures to be more flexible than a central body.

The components may be formed of biocompatible material. In some instances, the components may be formed of materials that may be designed to be reabsorbed into the body.

In some instances, any of the components may include antibiotics or growth factors that may be applied to the components and extrude from the components. In some instances, substances, such as antibiotics, antiviral or growth modulators, and growth factors may be distributed throughout the components so that they are constantly being extruded into the surrounding body, or that they are being extruded after a certain amount of time has passed. In some embodiments, the antibiotics or growth factor may be provided in materials that may gradually be reabsorbed by the body over time. As materials degrade or are absorbed, such treatments may be extruded. Such configurations may assist with the delayed or prolonged extrusion of particular antibiotics or growth factors.

For example, further during production or post-production, certain modulators may be used. These can be "given off" by a suture as it degrades. This may help improve healing or regard bacterial growth. Such wound modification techniques may assist with fibroid regrowth or the healing of various tissues. This may assist with preventing the development of a biofilm about the device. This may also help prevent infections or suture abscesses when the sternal device is applied.

In some embodiments, one or more components of the sternal device may be formed of a material that may become more malleable when warmed (e.g., Lactosorb). In such situations, after a device is positioned along a desired anatomical feature, such as a sternum, it may be heated up and pressed down to make it conform to the shape of the anatomical feature and/or make it more low profile (e.g., smooth out a higher part).

Method of Using Sternal Device

Any of the embodiments of a sternal device may be applied to a body. A method of connecting two tissues may include one or more of the following steps. A connection device may be provided where the connection device includes a central body and a plurality of male sutures. The central body may have a plurality of male stems, a plurality of female stems, and plurality of female bases connected to the female stems. Optionally, the central body may also have a plurality of male bases connected to the male stems. The male sutures may be connected to and extend from a male stem, whether it be directly from the male stem or indirectly via a male base. The male and female stems may extend from a common central point of the central body.

A first male suture may be wrapped around two tissues and may be connected to a first female base. In some embodiments, the two tissues may be bone tissue. The two tissues may form parts of a sternum. A second male suture may also be wrapped the two tissues, and may be connected to a second female base. The first male suture and/or the second male suture may be tightened to fit around the two tissues snugly. For instance, they may be tightened to finger-tightness. Optionally, they may be further tightened using a device or mechanism. In some embodiments, when the first and second male sutures are wrapped around the two tissues, they may cross one another. In other embodiments, they do not cross one another.

In some embodiments, in order to wrap around the two tissues, at least one of the first male suture or second male suture may pass through soft tissue. Preferably, the device will not be penetrating of bone-tissue.

In accordance with an aspect of the invention, one technique may include the following steps to position a sternal device around a sternum.

Figure 31A:
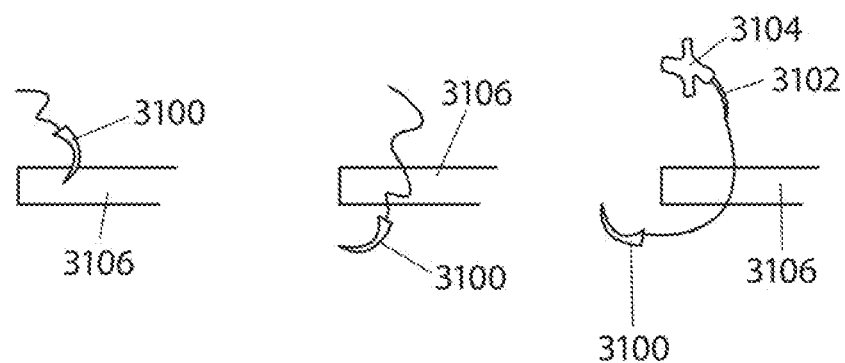
FIG. 31A shows a step for applying a sternal device in a body.

First, a standard needle driver may be used to pass the needle from an anterior side to a posterior side near a rib 3106 on a first side. The needle may be retrieved posterior and the device may be begun to be pulled through. FIG. 31A shows an example of a needle 3100 passing through. The needle may be attached to a suture 3102 which may be attached to a central body 3104. Alternatively, the suture itself may have an integral pointed end that may function as a needle. In some instances, the integrated pointed end may be formed of a harder or more rigid material than the rest of the suture.

Second, the male suture may be passed through the tissue lateral to the sternum near the rib in the same manner.

Third, both sutures may be pulled through to where the male base approaches the sternal-rib horizon. In some embodiments, the sutures may be pulled through so that one suture crosses over another suture. Alternatively, they may be pulled through so that they do not contact one another.

Figure 31B:
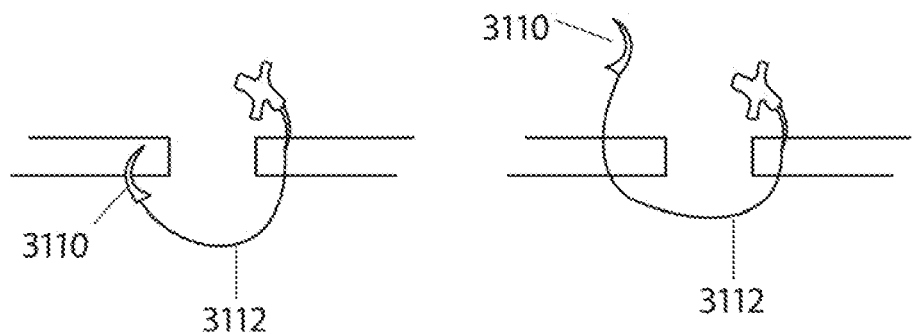
FIG. 31B shows another step for applying a sternal device in a body.

Fourth, the needle driver may be reapplied to the needle and the needle may be driven on a second side of the cut sternum in a posterior to anterior direction. FIG. 31B shows an example of this step. The needle 3110 may they be retrieved anterior and the suture 3112 may be pulled through. This act may be repeated for one or more sutures on the other side of the ipsilateral rib.

Next, the needle need not be cut off at or near the needle/engagement zone area and discarded. However, in some embodiments, the needle may be removed at this step.

The engagement zone of a first male suture may be fitted into an appropriate female base and engaged. Once engaged, it may not be reversed. The male suture may then be continuously engaged until the device is tightened to a desired degree. In other embodiments, the male suture is not engaged until the device is tightened to a desired degree. In some instances, the desired degree may be when the device is finger tight. A second suture and/or any other additional sutures may be engaged in this manner.

The central body may be properly positioned so that it is in good position on the sternum and not warped or twisted and the shaped body may lie congruent with the sternum. Optionally, the female base may be positioned near the rib/sternum horizon to limit the palpability of the female base.

The male suture may be engaged with force until the sternum is properly closed. The male suture may or may not be pulled by a tension gun or other device or mechanism to achieve closure.

Once the sternum is in a proper position and male engagement is tight, then excess male suture distal to the female base may be trimmed and discarded.

Figure 32A:
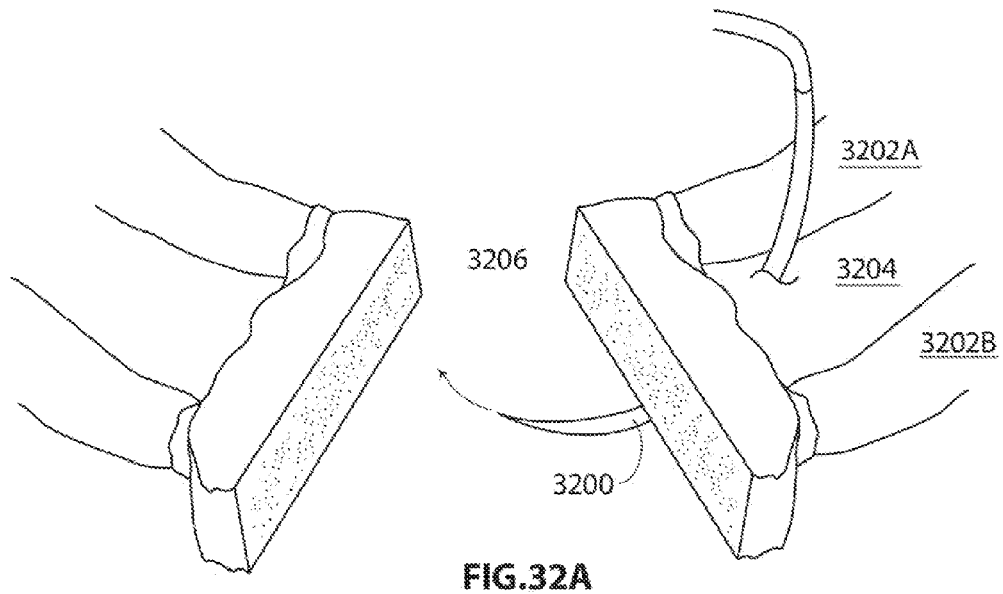
FIG. 32A illustrates a step for providing a sternum connecting device on a sternum.

In accordance with another embodiment of the invention, a technique for applying a sternum connecting device may be provided. A drive needle may be driven through intercostal tissue (which may be tissue between two ribs). In some embodiments, the drive needle may be attached to a suture. Alternatively, the drive needle may be an integral part of the suture, or may be a pointed end of the suture. FIG. 32A illustrates a needle 3200 being driven through tissue 3204 between two ribs 3202a, 3202b. This may assist with connecting a split sternum 3206.

Figure 32B:
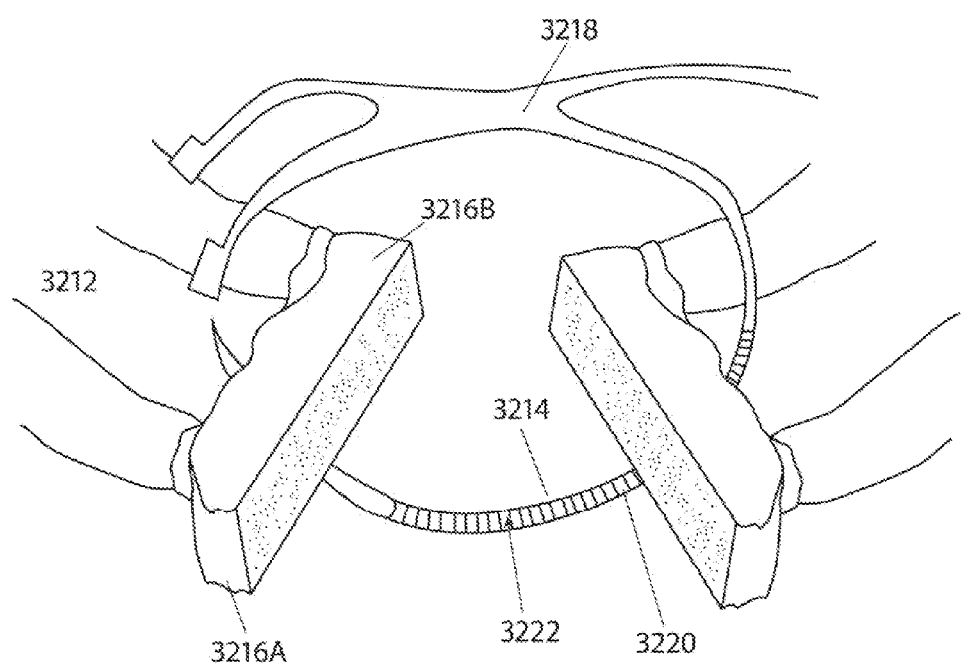
FIG. 32B illustrates an additional step to place a sternum connecting device on a sternum.

FIG. 32B illustrates an additional step to place a sternum connecting device on a sternum. The needle 3210 may be driven through intercostal tissue 3212 on the other side of the sternum. The suture 3214 may be drawn through the intercostal tissue on the first side and around a posterior side of the sternum 3216a. A central body 3218 may be positioned on an anterior side of the sternum 3216b. In alternate embodiments, the central body may be positioned on the posterior side of the sternum while the suture may be drawn around the anterior side of the sternum. The suture may include a locking zone 3220 and/or an engagement zone 3222 that may be attached to the needle.

Figure 32C:
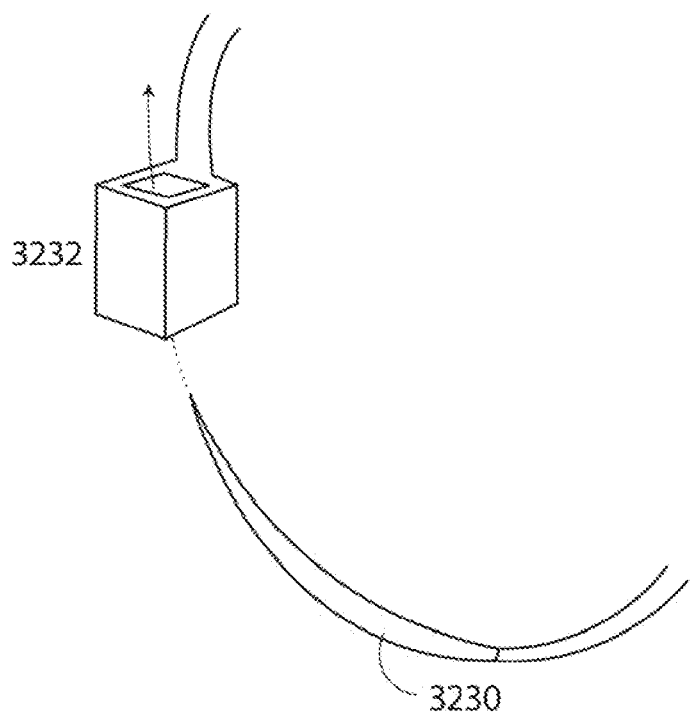
FIG. 32C illustrates how a sternum connecting device may be used to connect a sternum.

FIG. 32C illustrates how a sternum connecting device may be used to connect a sternum. In another step, the needle 3230 may be inserted through a female locking zone 3232 on a central body.

As a male suture is drawn through the female lock, an orientation feature (e.g., guiding channel molded into an engagement zone) may automatically orient the male locking features to the female locking features. In other embodiments, orientation features may not be needed and the male locking features may be able to engage with the female locking features, regardless of how the male suture is oriented.

The male suture may be passed through the female locking zone until the device is secure and the two halves of the sternum are closed. The male suture may be passed through to create a desired degree of tightness around the sternum.

Figure 32D:
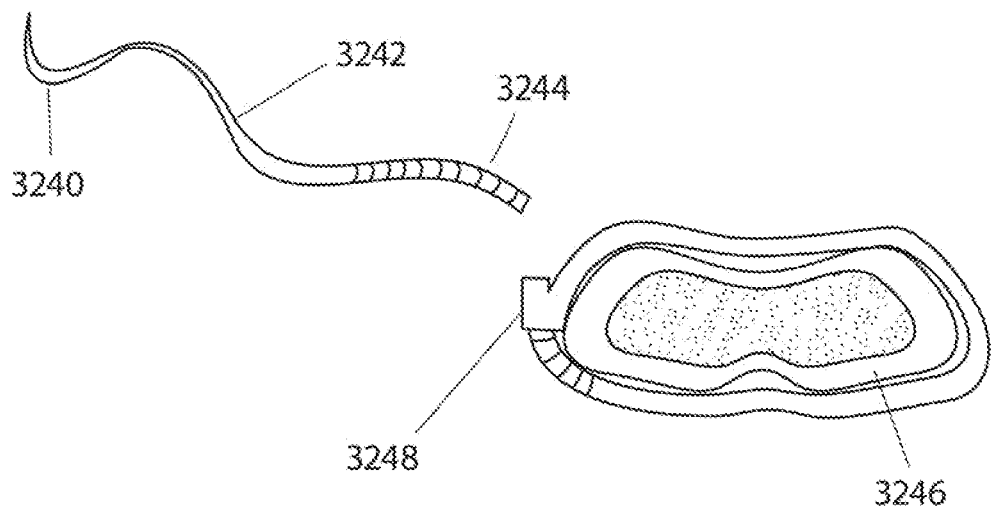
FIG. 32D illustrates a subsequent step for connecting a sternum using a sternum connecting device.

FIG. 32D shows how the needle 3240, engagement zone 3242, and any excess portion of the male locking zone 3244 may be trimmed off. For example, the device may be wrapped around the sternum 3246, and excess male suture may be cut off near the female lock 3248.

In accordance with some embodiments of the invention, such techniques may be applied with multiple sternal devices to capture multiple ribs. For example, in some embodiments, about four devices may be utilized. In such situations, all needles may be driven across one half of the sternum. For example, if four devices are used, and each device has two sutures, eight male sutures may be driven across a split sternum. Following that, each male suture may be inserted into its respective female locking zone. In alternate embodiments, each male suture may be driven across a split sternum and inserted into its respective female locking zone, one at a time. Alternatively, the order of these steps may be modified so that any number of sutures are driven across and inserted into a female locking zone.

Each suture may be hand tightened. The male suture may be pulled through as much as possible. At this point, the male locking zone may be engaged with the female locking zone. In alternate embodiments, a female retaining mechanism may be implemented to engage with a male suture, whether the male suture has a locking zone or not.

Figure 33:
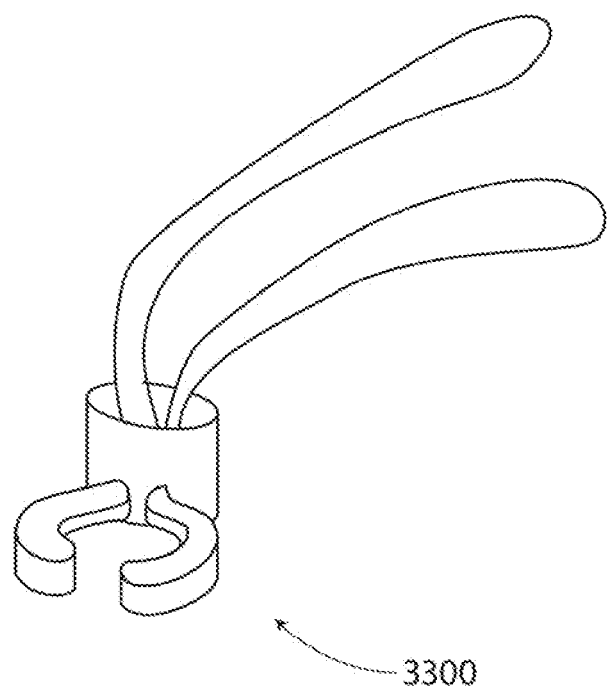
FIG. 33 shows a tensioning gun that may be used to tighten a sternum connecting device.

FIG. 33 shows a tensioning gun 3300 that may be used to tighten a sternum connecting device. The tensioning gun may be used to tighten a suture and/or cut it. In one implementation, the tensioning gun may include handles and jaws.

Figure 34:
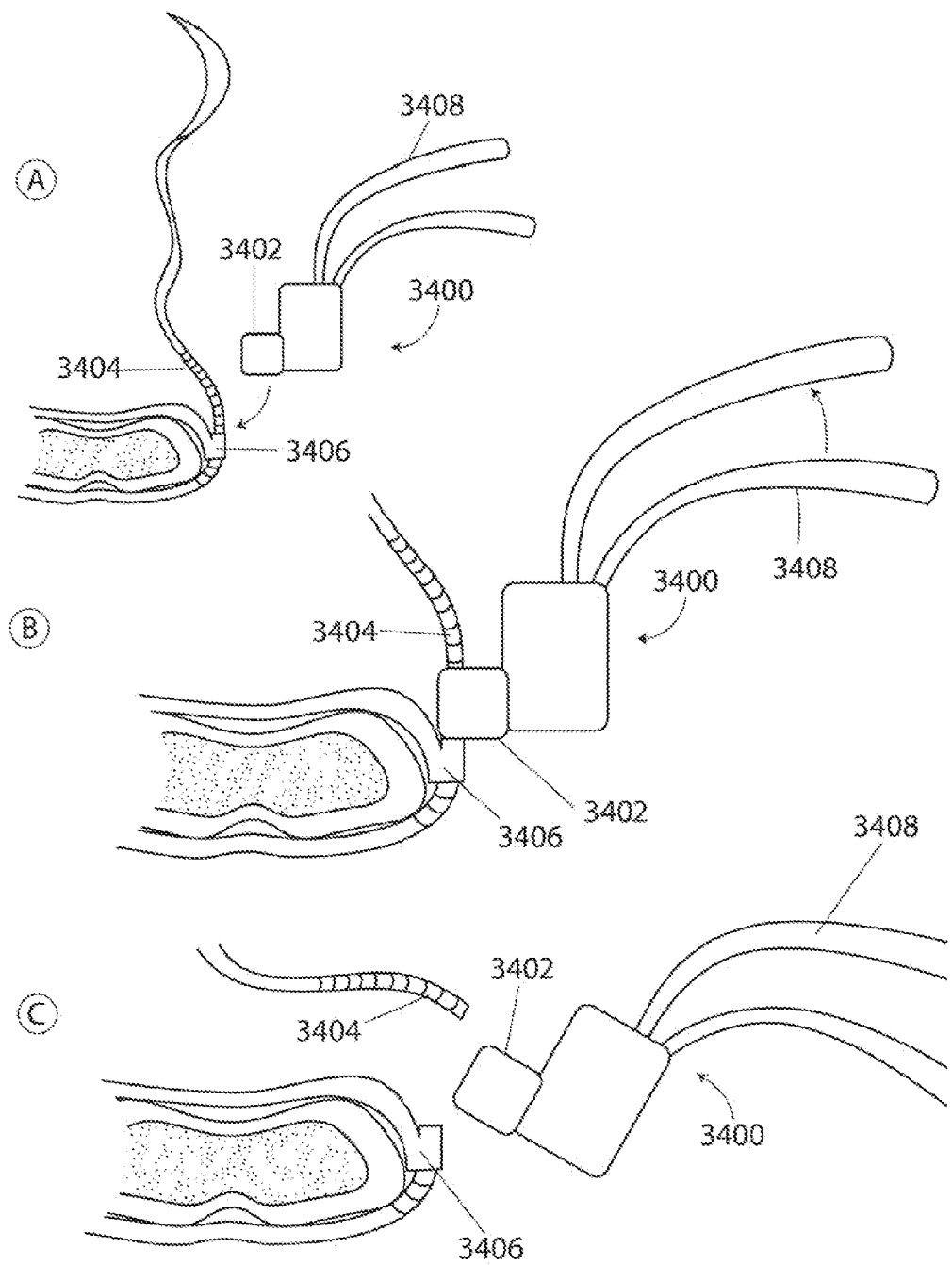
FIG. 34 shows how a tensioning gun may be used to tighten a sternum connecting device.

FIG. 34 shows how a tensioning gun 3400 may be used to tighten a sternum connecting device. As previously described, the jaws 3402 may close on the male suture 3404 beside the female lock 3406. The user may then squeeze the handles 3408. As the handles are squeezed together, the jaws may close on the male suture next to the female lock, pull it through a few more millimeters and then cut it. The handles may be squeezed to advance the suture in a ratchet-like fashion through the female lock. In some embodiments, the tensioning device may automatically cut the suture after the handles are squeezed. In other embodiments, other controls may be provided to cause the actual cutting step.

Sternal Device Kits

Another aspect of the invention further provides for a sternal device kit comprising the sternal device, which may comprise the central body and/or male sutures as discussed previously and instructions for use thereof. The kit may include one or more packages including one or more sternal device. The sternal devices may be disposable, so that they can be easily replaced after a given amount of use, or may have a one-time use. In some embodiments, various different sizes or configurations of sternal device may be available. Such varying sternal device configurations may allow a user to select an appropriate sternal device for a given subject or situation. In some embodiments, sternal devices may be individually packaged or may be packaged together.

The kit may also include a tool for placing the sternal device within a subject, such as a device to tighten the sternal device and/or cut off excess sutures. The kit may also include any tools that may be helpful to position the sternal device and/or penetrate soft tissue using a delivery needle. In some instances, a delivery needle and/or male suture may be provided as part of the sternal device, or separately from the sternal device. Furthermore, in other embodiments one or more stems may be provided as part of the central body of the sternal device, or may be provided separately to allow a user to select a stem to fit a desired subject. The devices or tools may include one or more components, which may or may not be included within the kit. Also, the various tools or devices, may be separate from the sternal device, and may or may not be included in the kit.

The kit may be conveniently packaged and may be commercially available. The kit may also include written, audio, or video instructions for use or maintenance of items therein.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method of closing two portions of a sternum, comprising:
    providing a connection device including:
        a central body with first and second flat male stems extending therefrom, and first and second flat female stems extending therefrom;
        a first flat, tape-like male suture engaged with and extending from the first male stem;
        a second flat, tape-like male suture engaged with and extending from the second male stem;
        a first curved delivery needle located on a distal end of the first male suture;
        a second curved delivery needle located on a distal end of the second male suture;
        a first flat, low-profile, sleeve-shaped female base connected to the first female stem by a first swivel connection structure that is configured to permit the first female base to swivel with respect to the first female stem, the first female base being configured to receive an end of the first male suture therethrough; wherein the first swivel connection structure includes a pin that connects the first female base to the first female stem; and
        a second flat, low-profile, sleeve-shaped female base connected to the second female stem by a second swivel connection structure that is configured to permit the second female base to swivel with respect to the second female stem, the second female base being configured to receive an end of the second male suture therethrough;
    inserting the first curved needle around the two portions of the sternum and wrapping the first male suture connected thereto around the two portions of the sternum;
    inserting the first male suture through the first female base;
    inserting the second curved needle around the two portions of the sternum and wrapping the second male suture connected thereto around the two portions of the sternum;
    inserting the second male suture through the second female base; and
    cutting off the first and the second curved needles from the first and the second male sutures.

2. The method of claim 1 wherein the male stems and the female stems extend from a common central portion of the central body.

3. The method of claim 1 further comprising tightening the first male suture to fit around the two portions of the sternum snugly, and tightening the second male suture to fit around the two portions of the sternum snugly.

4. The method of claim 1 further comprising allowing at least one of the first male suture or second male suture to pass through soft tissue.

5. The method of claim 1 further comprising cutting off excess male suture.

6. The method of claim 1 wherein the first male suture and the second male suture cross one another.

7. The method of claim 1 wherein at least one of the male stems or the female stems of the provided connection device is oriented at a non-parallel angle to another male stem or female stem.

8. The method of claim 1 wherein the first female base is not adjacent to a male base from which the first male suture extends.

9. The method of claim 1 wherein the first male suture crosses the second male suture when the first and second male sutures are received by their respective female bases.

10. The method of claim 1 wherein a first male suture of the provided connection device has an engagement zone which narrows the first male suture.

11. The method of claim 1 wherein the central body of the provided connection device has at least one hole.

12. The method of claim 1 wherein the male stems, female stems and male sutures of the provided connection device are integral to the central body.

13. The method of claim 1 wherein the female bases of the provided connection device are integrally formed on distal ends of the female stems.

14. The method of claim 1 wherein the central body of the provided connection device comprises multiple layers.

15. The method of claim 14 wherein the central body of the provided connection device is formed by two elongated stem pairs that cross over one another in a cross shape.

16. The method of claim 1 wherein the provided connection device is configured to form a cross shape on both a top and a bottom of a sternum when installed thereon.

17. The method of claim 1 wherein the central body, the female stems and the female bases of the provided connection device are configured such that when the central body is located on a front surface of a sternum, the female bases are located on a side of the sternum.

18. The method of claim 1 wherein the female bases of the provided connection device comprise retaining mechanisms configured to engage with male sutures that do not have locking zones.

19. The method of claim 1 wherein the stems are attached to one another such that an angle between them may be adjustable.

20. The method of claim 1, wherein the second swivel connection structure includes a pin that connects the second female base to the second female stem.

21. The method of claim 1, further comprising pivoting the first female base relative to the first female stem when inserting the first male suture through the first female base.

22. The method of claim 21, wherein pivoting the first female base includes pivoting the first female base within a restricted range.

23. The method of claim 1, further comprising pivoting the first male suture relative to the first male stem when inserting the first male suture through the first female base.

24. The method of claim 23, wherein pivoting the first male suture relative to the first male stem includes pivoting the first male suture within a restricted range.

25. The method of claim 1, further comprising pivoting the second female base relative to the second female stem when inserting the second male suture through the second female base.

26. The method of claim 1, further comprising pivoting the second male suture relative to the second male stem when inserting the second male suture through the second female base.

27. The method of claim 1, wherein the first male suture is engaged with the first male stem using a ball and socket joint that permits the first male suture to rotate relative to the first male stem.

28. The method of claim 27, wherein the second male suture is engaged with the second male stem using a ball and socket joint that permits the second male suture to rotate relative to the second male stem.

* * * * *